US011090106B2

(12) United States Patent
Wham et al.

(10) Patent No.: US 11,090,106 B2
(45) Date of Patent: Aug. 17, 2021

(54) CONTROL SYSTEMS FOR ELECTROSURGICAL GENERATOR

(71) Applicant: COVIDIEN LP, Mansfield, MA (US)

(72) Inventors: Robert H. Wham, Boulder, CO (US); Donald L. Tonn, Superior, CO (US); Aaron Mattmiller, Longmont, CO (US); William D. Faulkner, Boulder, CO (US); Edward L. Brannan, Erie, CO (US); Mark A. Johnston, Boulder, CO (US)

(73) Assignee: Covidien LP, Mansfield, MA (US)

( * ) Notice: Subject to any disclaimer, the term of this patent is extended or adjusted under 35 U.S.C. 154(b) by 860 days.

(21) Appl. No.: 15/098,822

(22) Filed: Apr. 14, 2016

(65) Prior Publication Data

US 2016/0310202 A1 Oct. 27, 2016

Related U.S. Application Data

(60) Provisional application No. 62/151,626, filed on Apr. 23, 2015.

(51) Int. Cl.
*A61B 18/12* (2006.01)
*A61B 18/00* (2006.01)

(52) U.S. Cl.
CPC ...... *A61B 18/1233* (2013.01); *A61B 18/1206* (2013.01); *A61B 2018/0072* (2013.01);
(Continued)

(58) Field of Classification Search
CPC ............ A61B 18/1206; A61B 18/1233; A61B 2018/00642; A61B 2018/00666;
(Continued)

(56) References Cited

U.S. PATENT DOCUMENTS

| 4,074,719 A | | 2/1978 | Semm | |
|---|---|---|---|---|
| 5,132,892 A | * | 7/1992 | Mizoguchi | H02M 7/49 363/41 |

(Continued)

FOREIGN PATENT DOCUMENTS

| DE | 179607 C | 3/1905 |
|---|---|---|
| DE | 390937 C | 3/1924 |

(Continued)

OTHER PUBLICATIONS

Wald et al., "Accidental Burns", JAMA, Aug. 16, 1971, vol. 217, No. 7, pp. 916-921.

(Continued)

*Primary Examiner* — Eun Hwa Kim
*Assistant Examiner* — Catherine C. Premraj
(74) *Attorney, Agent, or Firm* — Carter, DeLuca & Farrell LLP

(57) ABSTRACT

A controller for an electrosurgical generator includes an RF inverter, a signal processor, a software compensator, a hardware compensator, and an RF inverter controller. The RF inverter generates an electrosurgical waveform and the signal processor outputs a measured value of at least one of a voltage, a current, or power of the electrosurgical waveform. The software compensator generates a desired value for at least one of the voltage, the current, or the power of the electrosurgical waveform, and the hardware compensator generates a phase shift based on the measured value and the desired value. The RF inverter controller generates a pulse-width modulation (PWM) signal based on the phase shift to control the RF inverter.

20 Claims, 13 Drawing Sheets

(52) U.S. Cl.
CPC ............... *A61B 2018/0075* (2013.01); *A61B 2018/00642* (2013.01); *A61B 2018/00666* (2013.01); *A61B 2018/00767* (2013.01); *A61B 2018/00827* (2013.01); *A61B 2018/00892* (2013.01)

(58) Field of Classification Search
CPC .... A61B 2018/0072; A61B 2018/0075; A61B 2018/00767; A61B 2018/00827; A61B 2018/00892
See application file for complete search history.

(56) References Cited

U.S. PATENT DOCUMENTS

| | | | |
|---|---|---|---|
| 5,423,808 A * | 6/1995 | Edwards | A61B 18/12 606/34 |
| 6,142,992 A * | 11/2000 | Cheng | A61B 18/1206 606/34 |
| D574,323 S | 8/2008 | Waaler | |
| 8,303,580 B2 * | 11/2012 | Wham | A61B 18/1206 606/32 |
| 9,270,202 B2 | 2/2016 | Johnson et al. | |
| 9,283,028 B2 | 3/2016 | Johnson | |
| 2004/0111202 A1 * | 6/2004 | Mailer | A01B 79/005 701/50 |
| 2004/0167508 A1 | 8/2004 | Wham et al. | |
| 2005/0203504 A1 | 9/2005 | Wham et al. | |
| 2006/0006816 A1 * | 1/2006 | Alexandrov | H02M 7/538 315/291 |
| 2009/0196072 A1 * | 8/2009 | Ye | H02M 7/53871 363/17 |
| 2012/0215216 A1 * | 8/2012 | Friedrichs | A61B 18/1206 606/38 |
| 2012/0265195 A1 * | 10/2012 | Gilbert | H03H 17/0027 606/34 |
| 2013/0035679 A1 | 2/2013 | Orszulak | |
| 2013/0103023 A1 * | 4/2013 | Monson | H02J 7/00 606/33 |
| 2014/0232463 A1 | 8/2014 | Gilbert | |
| 2014/0243815 A1 | 8/2014 | Kerr | |
| 2014/0253140 A1 | 9/2014 | Gilbert | |
| 2014/0257270 A1 | 9/2014 | Behnke | |
| 2014/0258800 A1 | 9/2014 | Gilbert | |
| 2014/0276750 A1 | 9/2014 | Gilbert | |
| 2014/0276753 A1 | 9/2014 | Wham et al. | |
| 2014/0276754 A1 | 9/2014 | Gilbert et al. | |
| 2014/0358138 A1 | 12/2014 | Mattmiller et al. | |
| 2014/0376269 A1 | 12/2014 | Johnson et al. | |
| 2015/0025521 A1 | 1/2015 | Friedrichs et al. | |
| 2015/0025523 A1 | 1/2015 | Friedrichs et al. | |
| 2015/0032096 A1 | 1/2015 | Johnson | |
| 2015/0032098 A1 | 1/2015 | Larson et al. | |
| 2015/0032099 A1 | 1/2015 | Larson et al. | |
| 2015/0032100 A1 | 1/2015 | Coulson et al. | |
| 2015/0088116 A1 | 3/2015 | Wham | |
| 2015/0088117 A1 | 3/2015 | Gilbert et al. | |
| 2015/0088118 A1 | 3/2015 | Gilbert et al. | |
| 2015/0088124 A1 | 3/2015 | Wham | |
| 2015/0088125 A1 | 3/2015 | Wham | |
| 2015/0119871 A1 | 4/2015 | Johnson et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2602517 A1 | 7/1976 |
| DE | 2504280 A1 | 8/1976 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 3904558 A1 | 8/1990 |
| DE | 3942998 A1 | 7/1991 |
| DE | 4206433 A1 | 9/1993 |
| DE | 4339049 A1 | 5/1995 |
| DE | 19506363 A1 | 8/1996 |
| DE | 19717411 A1 | 11/1998 |
| DE | 19848540 A1 | 5/2000 |
| DE | 10 2008058737 A1 | 4/2010 |
| EP | 0 246 350 A1 | 11/1987 |
| EP | 267403 A2 | 5/1988 |
| EP | 296777 A2 | 12/1988 |
| EP | 310431 A2 | 4/1989 |
| EP | 325456 A2 | 7/1989 |
| EP | 336742 A2 | 10/1989 |
| EP | 0 556 705 A1 | 8/1993 |
| EP | 390937 A1 | 8/1993 |
| EP | 608609 A2 | 8/1994 |
| EP | 0 836 868 A2 | 4/1998 |
| EP | 880220 A2 | 11/1998 |
| EP | 0 882 955 A1 | 12/1998 |
| EP | 1051948 A2 | 11/2000 |
| EP | 1366724 A1 | 12/2003 |
| EP | 1776929 A1 | 4/2007 |
| FR | 1 275 415 A | 11/1961 |
| FR | 1 347 865 A | 1/1964 |
| FR | 2 313 708 A1 | 12/1976 |
| FR | 2364461 A1 | 4/1978 |
| FR | 2 502 935 A1 | 10/1982 |
| FR | 2 517 953 A1 | 6/1983 |
| FR | 2 573 301 A1 | 5/1986 |
| JP | 63 005876 A | 1/1988 |
| JP | 2002-065690 A | 3/2002 |
| JP | 2005-185657 A | 7/2005 |
| SU | 166452 | 1/1965 |
| SU | 727201 A2 | 4/1980 |
| WO | 02/11634 A1 | 2/2002 |
| WO | 02/45589 A2 | 6/2002 |
| WO | 03/090635 A1 | 11/2003 |
| WO | 06/050888 A1 | 5/2006 |
| WO | 08/053532 A1 | 5/2008 |

OTHER PUBLICATIONS

Vallfors et al., "Automatically Controlled Bipolar Electrosoagulation—'COA-COMP'", Neurosurgical Review 7:2-3 (1984) pp. 187-190.

Sugita et al., "Bipolar Coagulator with Automatic Thermocontrol", J. Neurosurg., vol. 41, Dec. 1944, pp. 777-779.

Prutchi et al. "Design and Development of Medical Electronic Instrumentation", John Wiley & Sons, Inc. 2005.

Momozaki et al. "Electrical Breakdown Experiments with Application to Alkali Metal Thermal-to-Electric Converters", Energy conversion and Management; Elsevier Science Publishers, Oxford, GB; vol. 44, No. 6, Apr. 1, 2003 pp. 819-843.

Muller et al. "Extended Left Hemicolectomy Using the LigaSure Vessel Sealing System", Innovations That Work; Company Newsletter; Sep. 1999.

"Electrosurgical Unit Analyzer ESU-2400 Series User Manual" Apr. 1, 2002; Retrieved from Internet: <URL:http//www.ocgroupintl.com/ESU_2400/Updates/ESU-2400_UM_Rev04.pdf>, pp. 6, 11, 73.

Ogden Goertzel Alternative to the Fourier Transform: Jun. 1993 pp. 485-487, Electronics World; Reed Business Publishing, Sutton, Surrey, BG vol. 99, No. 9. 1687.

Hadley I C D et al., "Inexpensive Digital Thermometer for Measurements on Semiconductors", International Journal of Electronics; Taylor and Francis. Ltd.; London, GB; vol. 70, No. 6 Jun. 1, 1991; pp. 1155-1162.

(56) References Cited

OTHER PUBLICATIONS

Richard Wolf Medical Instruments Corp. Brochure, "Kleppinger Bipolar Forceps & Bipolar Generator", 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy", Journal Neurosurgery, 83; (1995) pp. 271-276.
Geddes et al., "The Measurement of Physiologic Events by Electrical Impedence", Am. J. MI, Jan. Mar. 1964, pp. 16-27.
Cosman et al., "Methods of Making Nervous System Lesions", In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance", Applied Neurophysiology 51: (1988) pp. 230-242.
Zlatanovic M., "Sensors in Diffusion Plasma Processing" Microelectronics 1995; Proceedings 1995; 20th International conference CE on Nis, Serbia Sep. 12-14, 1995; New York, NY vol. 2 pp. 565-570.
Ni W. et al. "A Signal Processing Method for the Coriolis Mass Flowmeter Based on a Normalized . . . ", Journal of Applied Sciences—Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297, Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone", Neurosurgery 15: (1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300", 1 p. Sep. 1998.
Valleylab Brochure "Valleylab Electroshield Monitoring System", 2 pp. Nov. 1995.
U.S. Appl. No. 10/406,690, filed Apr. 3, 2003 inventor: Behnke.
U.S. Appl. No. 10/573,713, filed Mar. 28, 2006 inventor: Wham.
U.S. Appl. No. 11/242,458, filed Oct. 3, 2005 inventor: Becker.
European Search Report issued in corresponding EP Application No. 16 16 6699, dated Nov. 7, 2016, 8 pages.

\* cited by examiner

CONTROL SYSTEMS FOR ELECTROSURGICAL GENERATOR

CROSS-REFERENCE TO RELATED APPLICATION

The present application claims priority to and the benefit of U.S. Provisional Application No. 62/151,626 filed on Apr. 23, 2015, the entire contents of which are incorporated by reference herein.

BACKGROUND

1. Technical Field

The present disclosure relates to an electrosurgical system. More particularly, the present disclosure relates to electrosurgical generator control systems and methods for controlling a phase-shifted resonant inverter and/or high voltage direct current (DC) power supply of the electrosurgical generator.

2. Background of Related Art

Electrosurgery involves application of radio frequency (RF) alternating current (AC) to cut or modify biological tissue during an electrosurgical procedure. An electrosurgical generator, e.g., a power supply or waveform generator, generates the AC, which is applied to a patient's tissue through an active electrode and is returned to the electrosurgical generator through a return electrode.

During electrosurgery, the AC generated by the electrosurgical generator is conducted through tissue disposed between the active and return electrodes. The tissue's impedance converts the electrical energy, e.g., electrosurgical energy, associated with the AC into heat, which causes the tissue temperature to rise. The electrosurgical generator controls the treatment of the tissue by controlling various parameters of the AC supplied to the tissue. There is a need for an electrosurgical generator including improved control systems configured to precisely control energy delivery.

SUMMARY

The present disclosure features control systems for electrosurgical generators to control delivery of electrosurgical energy. In an embodiment, a controller for an electrosurgical generator includes an RF inverter, a signal processor, a software compensator, a hardware compensator, and an RF inverter controller. The RF inverter generates an electrosurgical waveform and the signal processor outputs a measured value of at least one of a voltage, a current, or power of the electrosurgical waveform. The software compensator generates a desired value for at least one of the voltage, the current, or the power of the electrosurgical waveform, and the hardware compensator generates a phase shift based on the measured value and the desired value. The RF inverter controller generates a pulse-width modulation (PWM) signal based on the phase shift to control the RF inverter.

In an aspect, the hardware compensator includes a setpointer configured to select a target value for at least one of the voltage, the current, or the power of the electrosurgical waveform, and a compensator configured to compensate for a first phase based on the target value. The compensator includes a proportional-integral-differential (PID) controller, which implements a second order PID algorithm. The compensator performs compensation for each period of the PWM signal.

In another aspect, the setpointer further determines a time when to switch the target value among a target voltage value, a target current value, and a target power value. The determined time is based on a measured value, and a maximum value of at least one of the voltage, the current, or the power of the electrosurgical waveform. The setpointer further prevents the RF electrosurgical energy from varying sufficiently before and after the target value is switched.

In yet another aspect, the hardware compensator further includes an impedance gain scheduler configured to calculate an impedance gain; a voltage gain scheduler configured to calculate a voltage gain; and a phase gain scheduler configured to calculate a phase gain. The hardware compensator further multiplies the first phase by the impedance gain and the voltage gain to obtain a second phase, and further multiplies the second phase by the phase gain to obtain a third phase.

In yet another aspect, the hardware compensator further includes a limiter configured to limit the third phase within a predetermined range.

In yet another aspect, the hardware compensator further includes an integrated error calculator configured to calculate an integrated error based on at least one of the impedance gain, the voltage gain, the phase gain, the second phase, and the third phase. The compensator further compensates for the first phase further based on the error between the desired value and the measured value of the target. The controller further includes a scale configured to scale the third phase and provide the scaled third phase to the RF inverter controller.

In yet another aspect, the hardware compensator is further configured to generate the phase shift for the RF inverter controller in response to an update signal from the RF inverter controller.

In still another aspect, the compensator further compares the desired value with the measured value.

In still another aspect, the software compensator is further configured to update the desired value in response to a change in impedance.

In still another aspect, the RF inverter is further configured to adjust average power of the electrosurgical waveform based on the phase shift, the phase shift being from about zero to about pi radian.

In still another aspect, the desired value and the measured value are root mean square (RMS) values.

In yet still another aspect, the signal processor further decimates and filters sensed voltage and current waveforms of the electrosurgical waveform to provide first and second path data to the software compensator.

In another embodiment, an electrosurgical generator includes an RF inverter, a plurality of sensors, a plurality of ADCs, and a controller. The RF inverter generates an electrosurgical waveform, the plurality of sensors is coupled to the RF inverter and senses a voltage waveform and a current waveform of the electrosurgical waveform, and the plurality of ADCs digitally samples the sensed voltage and current waveforms.

The controller is coupled to the plurality of ADCs and includes a signal processor, a software compensator, a hardware compensator, and an RF inverter controller. The signal processor outputs a measured value of at least one of a voltage, a current, or power of the electrosurgical waveform. The software compensator generates a desired value for at least one of the voltage, the current, or the power of the electrosurgical waveform, and the hardware compensator generates a phase shift based on the measured value and the desired value. The RF inverter controller generates a pulse-width modulation (PWM) signal based on the phase shift to control the RF inverter.

In yet another embodiment, an electrosurgical generator includes a power supply, a radio frequency (RF) inverter, a plurality of sensors, a plurality of analog-to-digital converters (ADCs), and a controller. The power supply outputs high voltage direct current (HVDC) power. The RF inverter is coupled to the power supply and generates an electrosurgical waveform, the plurality of sensors senses a voltage waveform and a current waveform of the electrosurgical waveform, and the plurality of ADCs digitally samples the sensed voltage and current waveforms.

The controller is coupled to the plurality of ADCs and includes a signal processor, a software compensator, a HVDC setpointer, and an RF inverter controller. The signal processor outputs a measured value of at least one of a voltage, a current, or power of the electrosurgical waveform. The HVDC setpointer sets a magnitude for the power supply. The RF inverter controller generates a PWM signal having a fixed phase to control the RF inverter.

In an aspect, the fixed phase is in a range where the RF inverter operates in zero voltage switching. The fixed phase is in a range where contribution of third and fifth harmonics is optimized with respect to the contribution of a fundamental of the PWM signal.

In another aspect, the signal processor calculates a phase shift and compares the phase shift with the fixed phase. The HVDC setpointer decreases the desired value for the HVDC power when the phase shift is less than the fixed phase, and increases the desired value for the HVDC power when the phase shift is greater than the fixed phase.

BRIEF DESCRIPTION OF THE DRAWINGS

Various embodiments of the present disclosure are described with reference to the accompanying drawings wherein.

DETAILED DESCRIPTION

The present disclosure provides an electrosurgical generator, a phase-shifted resonant inverter, a high voltage DC power supply, a hardware compensator, and a software compensator embodied in a controller for controlling output of the resonant inverter and the power supply. The resonant inverter includes a plurality of switching components, e.g., MOSFETs, controlled by PWM signals. In particular, the hardware compensator controls and adjusts phase shift of the PWM signals supplied to the resonant inverter based on various tissue and energy data, e.g., voltage, current, power, and the impedance of treated tissue. The hardware compensator controls the phase shift faster than the software compensator, while the software compensator outputs results having greater accuracy than the hardware compensator does.

Figure 1:
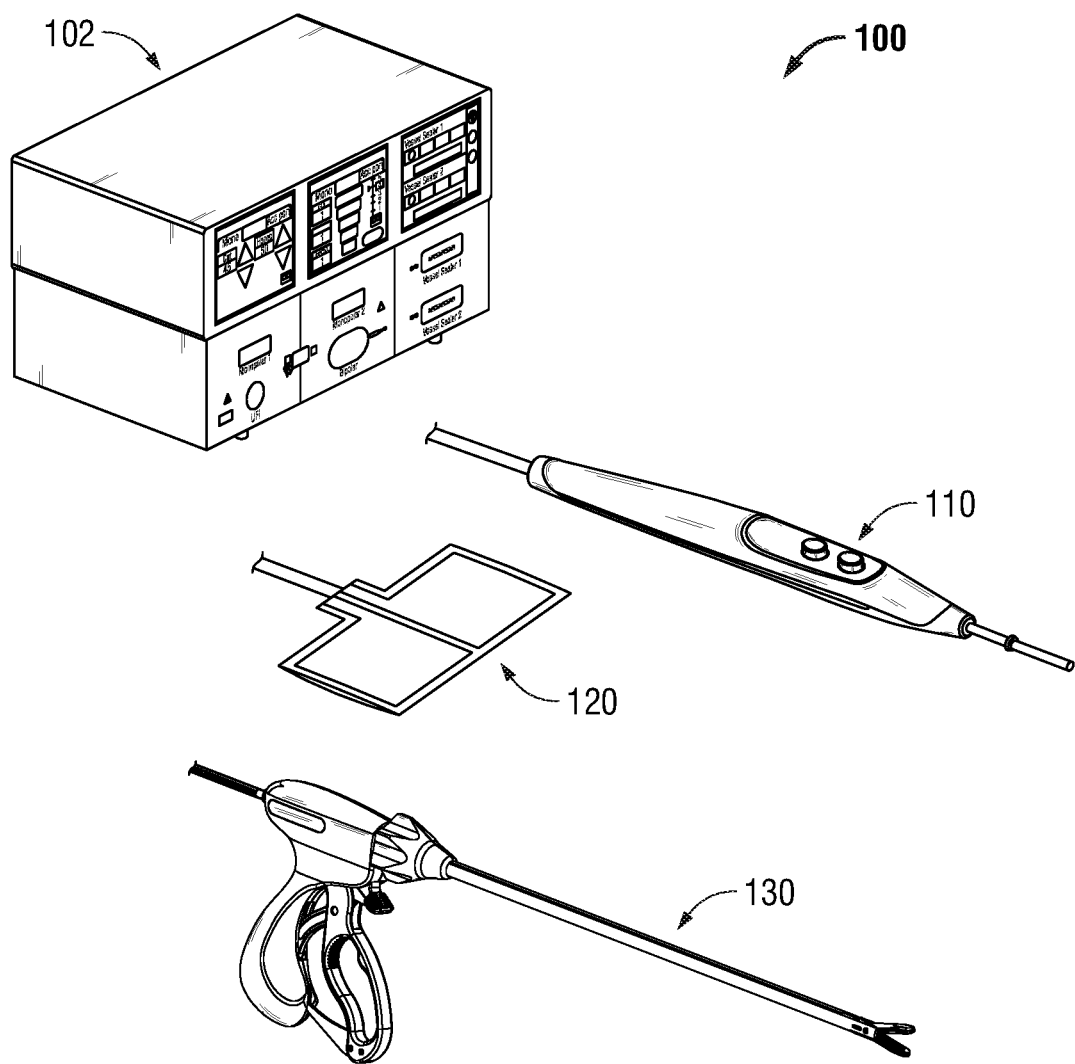
FIG. 1 is a perspective view of an electrosurgical system in accordance with embodiments of the present disclosure.

FIG. 1 illustrates an electrosurgical system 100 in accordance with embodiments of the present disclosure. The electrosurgical system 100 includes an electrosurgical generator 102 which generates electrosurgical energy for treating tissue of a patient. The electrosurgical generator 102 generates electrosurgical energy at an appropriate level based on the selected mode of operation (e.g., cutting, coagulating, ablating, or sealing), the sensed voltage and current waveforms of the electrosurgical energy, measured tissue properties, and combinations thereof. The electrosurgical generator 102 may also include a plurality of output connectors for coupling the electrosurgical generator 102 a variety of electrosurgical instruments.

The electrosurgical system 100 may include a monopolar electrosurgical instrument 110 having an electrode for treating tissue of the patient (e.g., an electrosurgical cutting probe, also known as an electrosurgical pencil, or an ablation electrode) with a return pad 120. The monopolar electrosurgical instrument 110 can be connected to the electrosurgical generator 102 via one of the plurality of output connectors. The electrosurgical energy is supplied to the monopolar electrosurgical instrument 110, which applies the electrosurgical energy to treat the tissue. The electrosurgical energy is returned to the electrosurgical generator 102 through the return pad 120. The return pad 120 provides a sufficient contact area with the patient's tissue so as to minimize the risk of tissue damage due to the electrosurgical energy applied to the tissue.

The electrosurgical system 100 may also include a bipolar electrosurgical instrument 130 including a pair of opposing jaw members. The bipolar electrosurgical instrument 130 can be connected to the electrosurgical generator 102 via one of the plurality of output connectors. The electrosurgical energy is supplied to one of the two jaw members, is applied to treat the tissue, and is returned to the electrosurgical generator 102 through the other jaw member.

As noted above, the electrosurgical generator 102 may also be configured to operate in a variety of modes, such as ablation, cutting, coagulation, and sealing. The electrosurgical generator 102 may include a switching mechanism (e.g., relays) to switch the supply of RF energy among the connectors to which various electrosurgical instruments may be connected. In embodiments, the electrosurgical generator 102 may be configured to provide RF energy to a plurality instruments simultaneously.

In further embodiments, the electrosurgical generator 102 may include a user interface having suitable user controls (e.g., buttons, activators, switches, or touch screens) for providing control parameters to the electrosurgical generator 102. These controls allow the user to adjust parameters of the electrosurgical energy (e.g., the power level or the shape of the output waveform) so that the electrosurgical energy is suitable for a particular electrosurgical mode (e.g., coagulating, ablating, tissue sealing, or cutting). The electrosurgical instruments 110 and 130 may also include a plurality of user controls. In addition, the electrosurgical generator 102 may include one or more display screens for displaying a variety of information related to operation of the electrosurgical generator 102 (e.g., intensity settings and treatment complete indicators).

Figure 2:
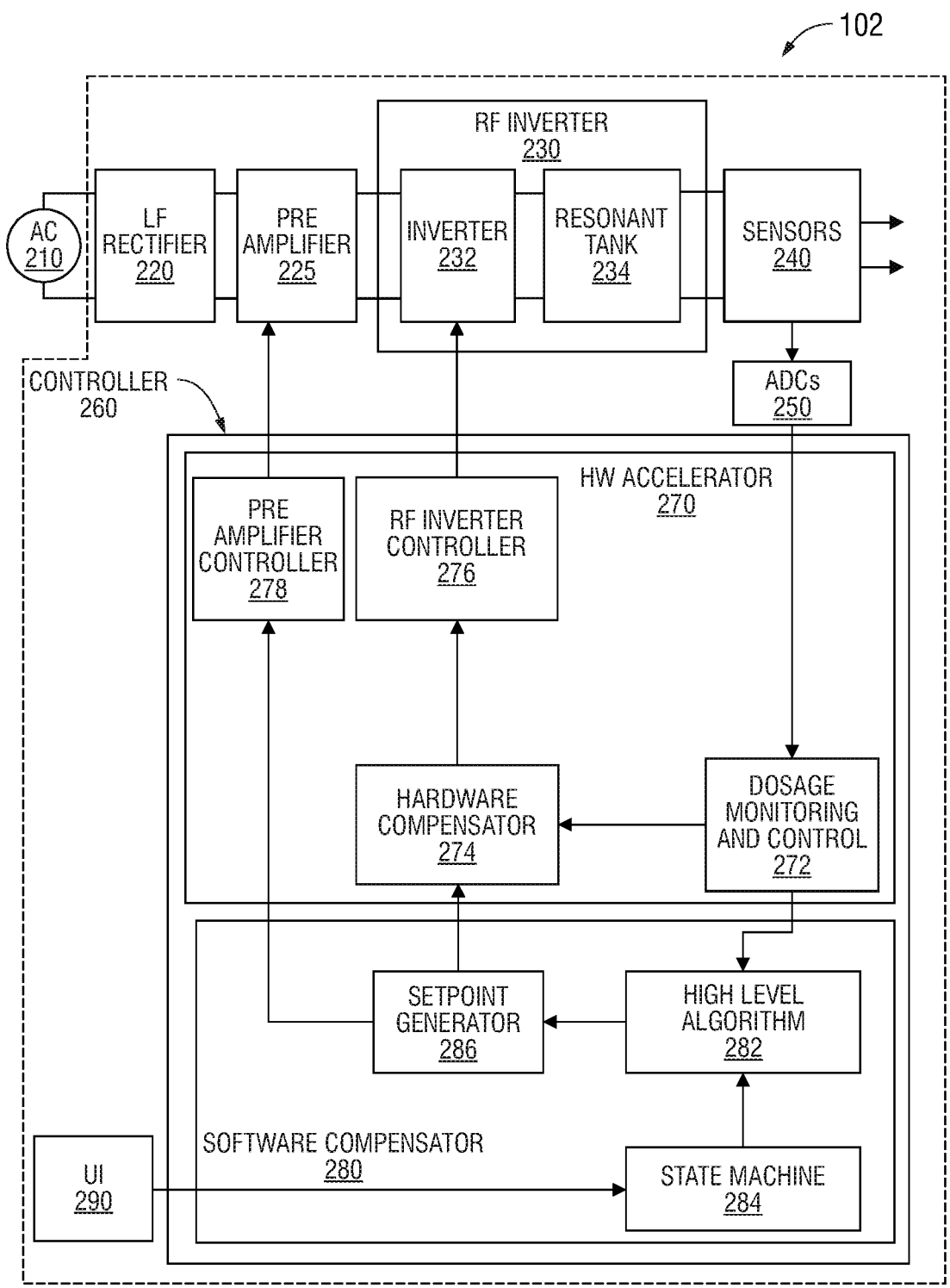
FIG. 2 is a block diagram of an electrosurgical generator of the electrosurgical system of FIG. 1 in accordance with embodiments of the present disclosure.

FIG. 2 is a block diagram of the electrosurgical generator 102 of FIG. 1. The electrosurgical generator 102 includes a low frequency (LF) rectifier 220, a preamplifier 225, an RF inverter 230, a plurality of sensors 240, analog-to-digital converters (ADCs) 250, a controller 260, and a user interface (UI) 290. The electrosurgical generator 102 is configured to connect to an alternating current (AC) power source 210, such as a wall power outlet or other power outlet, which generates AC having a low frequency (e.g., 25 Hz, 50 Hz, or 60 Hz). The AC power source 210 provides AC power to the LF rectifier 220, which converts the AC to direct current (DC).

The direct current (DC) output from the LF rectifier 220 is provided to the preamplifier 225, which amplifies the DC to a desired level. The amplified DC is provided to the RF inverter 230, which includes an inverter 232 and a resonant tank 234.

In embodiments, the electrosurgical generator 102 may be battery-powered. Since the battery provides DC power to the electrosurgical generator 102, the electrosurgical generator 102 may not have to include the LF rectifier 220. Further, the electrosurgical generator 102 may be incorporated into the electrosurgical instruments 110 and 130 so that the electrosurgical generator 102 and the electrosurgical instruments do not need wires and thus may be portable.

The inverter 232 inverts the amplified DC waveform to an AC waveform having a frequency suitable for an electrosurgical procedure, which may be from about 100 kHz to about 1,000 kHz, and in certain embodiments from about 200 kHz to about 500 kHz. The appropriate frequency of the AC waveform may differ based on the desired electrosurgical procedure and modes of electrosurgery. For example, nerve and muscle stimulations cease at about 100,000 cycles per second (100 kHz) above which point some electrosurgical procedures can be performed more optimally, i.e., the electrosurgical energy can pass through a patient to targeted tissue with minimal neuromuscular stimulation. In an aspect, typically ablation procedures may use a frequency of about 472 kHz. The inverter 232 also filters square waves to produce sinusoid waves, which increases amplitude as a phase shift is increased.

The resonant tank 234 is coupled to the output of the inverter 232 and is configured to match the impedance at the inverter 232 to the impedance of the tissue to provide for optimal power transfer between the electrosurgical generator 102 and the tissue.

The electrosurgical energy inverted by the inverter 232 is controlled by the controller 260. The voltage and current waveforms of the electrosurgical energy output from the inverter 232 are sensed by the plurality of sensors 240 and are provided to the controller 260, which, in turn, generates control signals to control the output of the preamplifier 225 and the output of the inverter 232. The control signals may be PWM signals or phase-shifted PWM signals. The controller 260 also receives input signals via the user interface (UI) 290. The UI 290 allows a user to select a type of electrosurgical procedure (e.g., monopolar or bipolar), a particular electrosurgical mode (e.g., coagulation, ablation, sealing, or cutting), and/or input desired control parameters for the electrosurgical procedure or the mode.

The plurality of sensors 240 sense voltage and current at the output of the RF inverter 230. The plurality of sensors 240 may include two or more pairs or sets of voltage and current sensors to provide redundant measurements. Use of redundant sensors prevents dosage error of the RF inverter 230, such as due to failure or faulty readings from a single set of sensors. In embodiments, the plurality of sensors 240 may include fewer or more sets of voltage and current sensors depending on the application or the design requirements. The plurality of sensors 240 may also measure the voltage and current output of other components of the electrosurgical generator 102, such as the inverter 232 or the resonant tank 234. The plurality of sensors 240 may include any known technology for measuring voltage and current including, for example, a Rogowski coil.

The sensed voltage and current waveforms are fed to analog-to-digital converters (ADCs) 250. The ADCs 250 sample the sensed voltage and current waveforms to obtain digital samples of the voltage and current waveforms. The digital samples of the voltage and current waveforms are processed by the controller 260 and are configured to generate control signals for controlling the inverter 232 of the RF inverter 230 and the preamplifier 225. The ADCs 250 may be configured to sample the sensed voltage and current waveforms at a sample period that is an integer multiple of the RF frequency.

With continued reference to FIG. 2, the controller 260 includes a hardware accelerator 270 and a software compensator 280. As described above, the controller 260 is also coupled to a UI 290, which receives input commands from a user and displays input and output information related to characteristics of the electrosurgical energy (e.g., selected power level). The hardware accelerator 270 processes the output from the ADCs 250 and cooperates with the software compensator 280 to generate control signals as described in further detail below.

The hardware accelerator 270 is configured to adjust PWM characteristic for the RF inverter 230 so that the desired RF output is reached as quickly as possible, while the software compensator 280 is designed to determine and adjust the set points for the hardware compensator 274 including, but not limited to, the voltage, the current, the power, and combinations thereof. In an aspect, the set points may be desired maximum values for the RMS voltage and current, the average power and RMS values of other parameters. In another aspect, the set points may be desired maximum values for peak voltage and current, peak average power, and peak or maximum values of other parameters. In yet another aspect, the set points may be target values for the voltage, current, power, and other parameters.

In yet another aspect, the set points for the voltage, current, power, and other parameters may be set via the UI 290. The software compensator 280 then determines set points for the voltage, current, and power based on the measured values for the voltage, current and power provided from the hardware accelerator 270, and passes the set points for the voltage, current, and power to the hardware accelerator 270.

In embodiments, the hardware accelerator 270 may use peak values of the voltage, current and power to limit arc initiation when a crest factor varies over the operating range due to harmonic distortion inherent in the phase-shift PWM controlling scheme. The arc may be prevented by placing a limit on the peak voltage below a predetermined value. In an aspect, a peak current may also be used to limit the arc when the peak current suddenly increases.

The crest factor of the voltage may be calculated by dividing the peak voltage by the RMS voltage. The crest factor decreases for a given RMS setpoint when the discontinuous RF duty cycle increases and vice versa. Further, when the crest factor decreases for a given peak voltage, RMS values for voltage, current, and average power increase. In an aspect, the hardware accelerator 270 may control the RF inverter 230 by controlling the crest factor. A more detailed description of controlling the crest factor can be found in U.S. patent application Ser. No. 12/401,981 filed on Mar. 11, 2009, and entitled "Crest Factor Enhancement in Electrosurgical Generators," the entire contents of which are incorporated by reference herein.

The hardware accelerator 270 includes dosage monitoring and control (DMAC) 272, a hardware compensator 274, an RF inverter controller 276, and a preamplifier controller 278. All or a portion of the controller 260 may be implemented by a field programmable gate array (FPGA), an application specific integrated circuit (ASIC), a digital signal processor (DSP), a microcontroller, or any other suitable logic device.

The DMAC 272 receives digital samples of the voltage and current waveforms from the ADCs 250 and calculates the average power, the voltage, the current, impedance of the tissue, or any other tissue or energy parameter as described in greater detail below. In an aspect, the DMAC 272 may decimate and filter the sensed voltage and current waveforms from the ADCs 250 and provide fast path data to the hardware compensator 274, and decimate and filter the sensed voltage and current waveforms from the ADCs 250 and provide slow path data to the software compensator 280. As used herein the terms "slow path" and "fast path" data denotes measured values for the power, the voltage, the current, the impedance of the tissue, and the like. The slow path data is more accurate than the fast path data, but having a larger time delay and a lower decimation rate than the fast path data, because the slow path data has more processes to compensate for the internal and external cable impedances.

The hardware compensator 274 receives the fast path data and generates a control signal for the RF inverter controller 276 in response thereto. In an aspect, the impedance of the tissue of the fast path data may be a real part of the tissue impedance. After receiving the control signal, the RF inverter controller 276, in turn, generates a first pulse-width modulation (PWM) control signal to control the output of the inverter 232. The control signal generated by the hardware compensator 274 may be a phase shift $\varphi_s$ signal for the RF inverter 230. The PWM control signal may be generated based on the phase shift. The phase shift $\varphi_s$ is further described with respect to FIGS. 4A and 4B below.

The software compensator 280 includes a high level algorithm 282, a state machine 284, and a setpoint generator 286. The software compensator 280 receives slow path data from the DMAC 272 and generates another control signal based on the slow path data. The software compensator 280 further receives parameters set via the UI 290, which may be an electrosurgical mode and target values for the voltage, the current, and the power. The parameters selected by a user are provided to the state machine 284, which determines a state or mode of the electrosurgical generator 102.

The high level algorithm 282 uses this state information and the output from the DMAC 272 to determine control data. The setpoint generator 286 receives the control data, generates the set points for the voltage, the current, and the power based on the control data. In particular, the setpoint generator 286 determines the current, power and voltage setpoints and/or limits as well as the desired output from the UI 290 and the high level algorithm 282. The set points may include, but are not limited to, the upper limits for the voltage, current, and the power, or for the peak voltage, peak current, and peak power. By adjusting the set points in real time, appropriate upper limits for the voltage, current, and power can be set as impedance changes. The set points may also adjust to deliver accurate energy to the patient since the hardware compensator 274 does not have access to the more accurate slow path sensor data.

The preamplifier controller 278 of the hardware accelerator 270 received the set points to generate an appropriate PWM control signal for controlling the preamplifier 225 to amplify the DC output from the LF rectifier 220 to a desired level. If the user does not provide operational parameters to the state machine 284 via the UI 290, then the state machine 284 may enter and maintain a default state. In an aspect, the preamplifier controller 278 may be implemented in the software compensator 280.

Figure 4A:
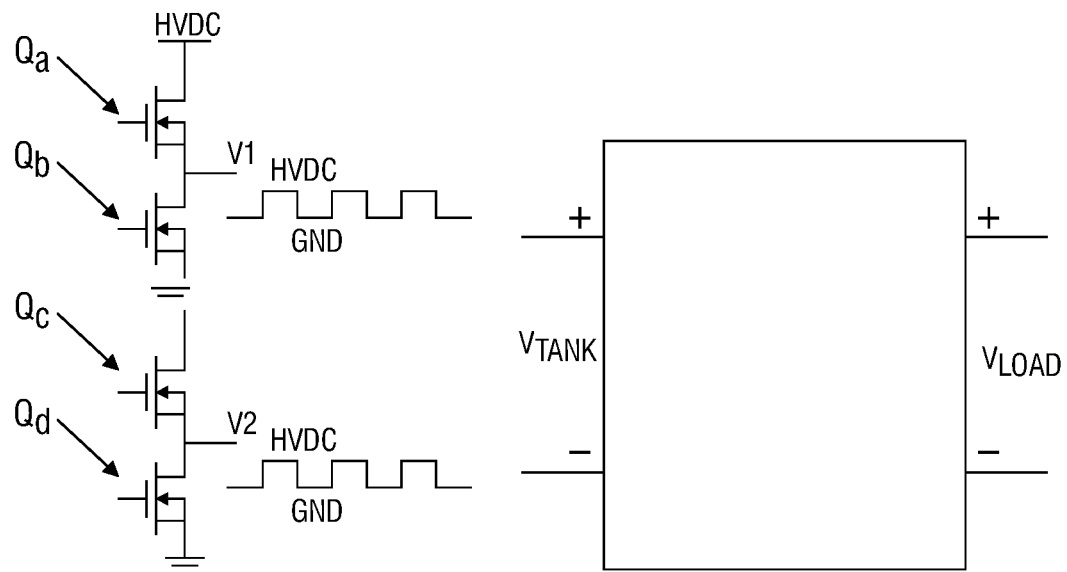
FIG. 4A is a graphical illustration of pulse width modulated (PWM) signals supplied to an RF inverter based on a phase shift in accordance with embodiments of the present disclosure.

FIG. 4A shows a circuit diagram for the inverter 232 and a block diagram for the resonant tank 234. The inverter 232 may be a full H-bridge including four switches, $Q_a$, $Q_b$, $Q_c$, and $Q_d$ having a switching frequency of $\omega_s$. The switches $Q_a$, $Q_b$, $Q_c$, and $Q_d$ invert high voltage direct current (HVDC) from the preamplifier 225. Switches $Q_a$ and $Q_b$ are electrically coupled to the positive input to the resonant tank 234 and provide voltages to the positive input, and switches $Q_c$ and $Q_d$ are electrically coupled to the negative input and provide voltages to the negative input to the resonant tank 234. The voltage output from switches $Q_c$ and $Q_d$ are phase-shifted based on the phase shift $\varphi_s$ from the RF inverter controller 276. The resonant tank 234 multiplies the voltage output from the switches $Q_c$ and $Q_d$ and adds to the voltage output from the switches $Q_a$ and $Q_b$. The resulting waveform is transferred to the tissue to be treated.

Figure 4B:
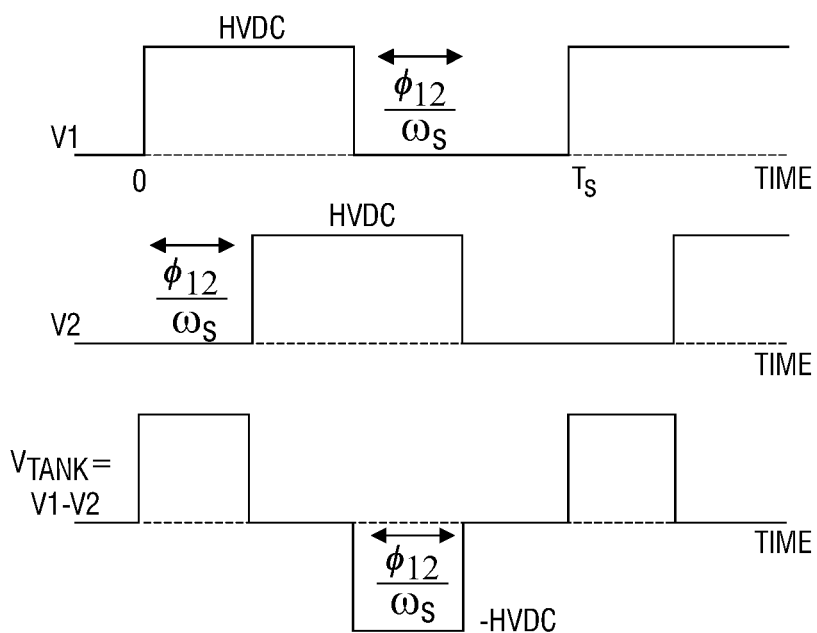
FIG. 4B is a graphical illustration of output voltages of the RF inverter based on a phase shift in accordance with embodiments of the present disclosure.

FIG. 4B shows graphical diagrams illustrating voltages of the positive and negative inputs and voltage of the resonant tank 234 of FIG. 4B. Top graph shows voltage $V_1$ supplied to the positive input of the resonant tank 234, which has a square wave having a magnitude of HVDC. The square wave rises up at the start of time, i.e., time=0, falls down at a half of a period $T_s$, and rises up again at the end of the period, i.e., the period=$T_s$.

The middle graph shows voltage $V_2$ supplied to the negative input of the resonant tank 234, which has a square wave having a magnitude of HVDC and is shifted by a phase $\varphi_{12}$, which is equal to the phase shift $\varphi_s$ received from the RF inverter controller 276. Since the phase is related with the switching frequency $\omega_s$, the voltage waveform is shifted in time by $$\frac{\phi_{12}}{\omega_s},$$

where the switching frequency $\omega_s$ is equal to $$\frac{2\pi}{T_s}.$$

The bottom graph shows voltage $V_{tank}$ based on subtraction of the voltages $V_1$ and $V_2$ shown in the middle graph. Due to the phase shift $\varphi_{12}$, the voltage $V_{tank}$ has a positive portion and a negative portion. Each portion has a magnitude of HVDC, which is the output of the preamplifier 225, and the temporal duration of $$\frac{\phi_{12}}{\omega_s},$$

such that, the DC power provided by the preamplifier 225 is inverted to the AC power having an appropriate level of the voltage, current, or power. As apparent in FIG. 4B, the duty cycle is directly proportional to the phase shift $\varphi_{12}$. The output of the inverter 232 (e.g., current, voltage, and power) is also proportional to the duty cycle, but not directly proportional.

Figure 3:
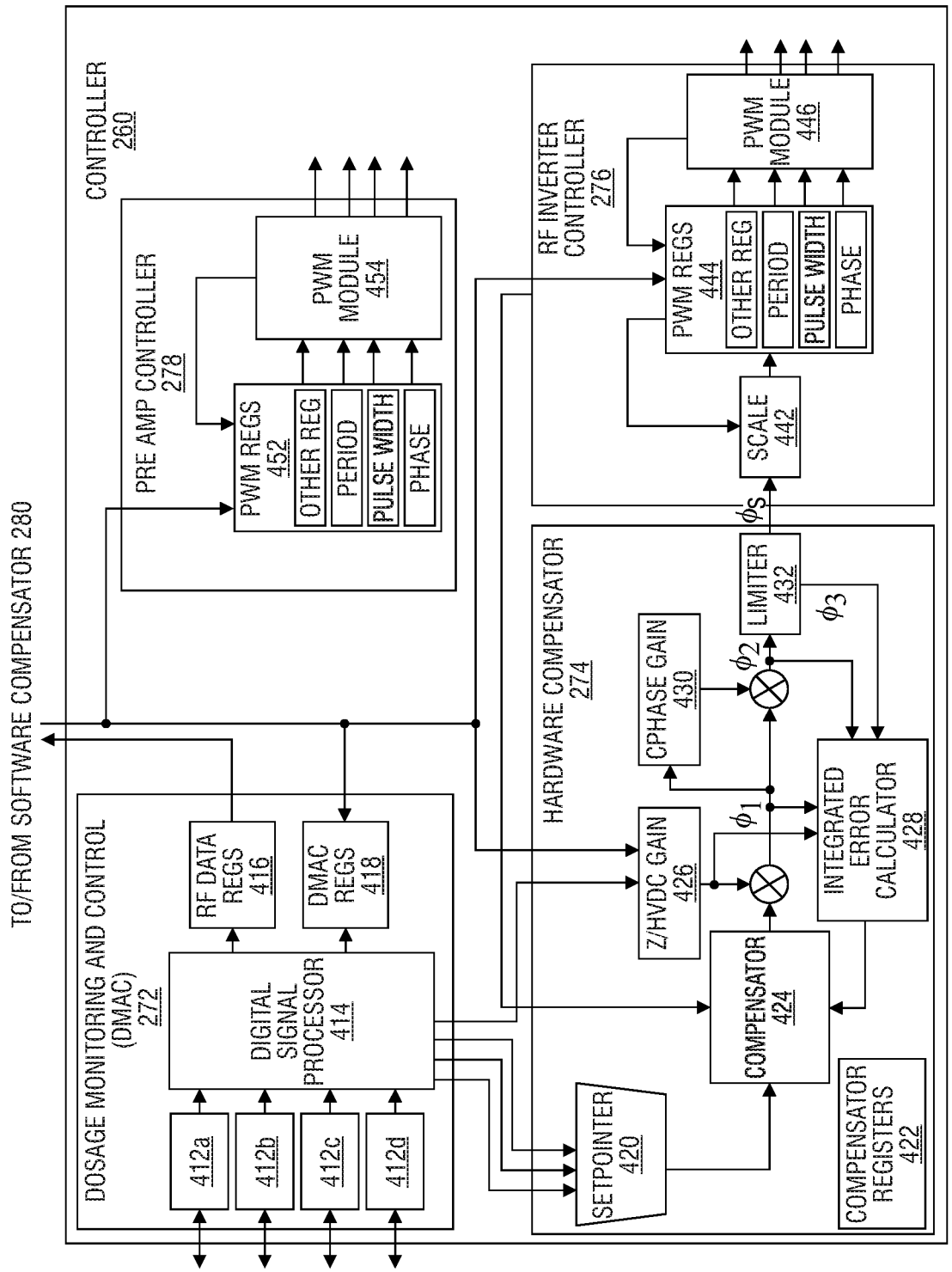
FIG. 3 is a schematic diagram of a controller of the electrosurgical generator of FIG. 2 in accordance with embodiments of the present disclosure.

FIG. 3 shows a detailed diagram of the hardware accelerator 270 of FIG. 2. The hardware accelerator 270 implements those functions of the electrosurgical generator 102 that may have special processing requirements, e.g., higher processing speeds. The hardware accelerator 270 includes the DMAC 272, the hardware compensator 274, the RF inverter controller 276, and the preamplifier controller 278, which includes PWM registers 452 and a PWM module 454.

The DMAC 272 includes four analog-to-digital converter (ADC) controllers 412a-412d, a digital signal processor 414, RF data registers 416, and DMAC registers 418. The ADC controllers 412a-412d control the operation of the ADCs 250, which samples digital data from sensed voltage and current waveforms. The digital data is then provided to the digital signal processor 414 that implements various filtering and other digital signal processing functions, some of which are described in more detail below.

The sensed voltage and current are input to the ADCs 250, which sample the sensed voltage and current. The ADC controllers 412a-412d provide operational parameters, including a predetermined sampling rate, to the ADCs 250 so that the ADCs sample the sensed voltage and current synchronously at a predetermined sampling rate, i.e., a predetermined number of samples per second, or predetermined sampling period. The ADC controllers 412a-412d may be configured to control the ADCs 250 so that the sampling period corresponds to an integer multiple of the RF frequency of the voltage and current waveforms.

The digital data obtained by sampling the voltage and current waveforms is provided to the digital signal processor 414 via the ADC controllers 412a-412d. The digital signal processor 414 uses the digital data to calculate voltage, current, power, and impedance, such as RMS voltage ($V_{rms}$), RMS current ($I_{rms}$), power, e.g., average power ($P_{avg}$), and the impedance $Z_{re}$ of treated tissue. The RMS voltage $V_{rms}$ and RMS current $I_{rms}$ are calculated according to the following formulas (1) and (2):

$$V_{rms} = \sqrt{avg(V^2)} \tag{1}$$

$$I_{rms} = \sqrt{avg(I^2)} \tag{2},$$

where V represents the samples of the voltage waveform, I represents samples of the current waveform, and "avg( )" represents an averaging function. The digital signal processor 414 uses averaging filters in calculating an average value of the real power. The average power $P_{avg}$ and the impedance $Z_{re}$ are then calculated according to the following formulas (3a), (3b), and (4):

$$P_{avg} = V_{rms} \times I_{rms} \times \cos\phi, \tag{3a}$$

$$P_{avg} = avg(V \times I), \text{ and} \tag{3b}$$

$$Z_{re} = \frac{V_{rms}}{I_{rms}} \times \cos\phi, \tag{4}$$

where $\varphi$ is the phase angle between the sampled voltage and current waveforms. When the phase angle $\varphi$ between the sampled voltage and current waveforms is calculated, the average power $P_{avg}$ can be calculated based on the formula (3a). Based on the formula (3b), the average power $P_{avg}$ is calculated by multiplying each voltage and current sample together and averaging the result.

Formulas (5a)-(5c) below are used for determining the impedance:

$$Z = \frac{V_{rms}}{I_{rms}}, \tag{5a}$$

$$Z = \frac{V_{rms}^2}{P}, \text{ and} \tag{5b}$$

$$Z = \frac{P}{I_{rms}^2}, \tag{5c}$$

where P is power. The formula (5a) may be used when power is used to control an electrosurgical operation, the formula (5b) may be used when voltage is used to control the operation, and the formula (5c) may be used when the current is used to control the operation. In an aspect, for slow path calculation, the impedance may be also calculated from narrow band data, which may be filtered by a FFT or Goertzel filter at specific frequencies for cable compensation.

Peak voltage is the maximum or minimum of the AC voltage waveform, and peak current is the maximum or minimum of the current waveform. Peak values may ideally be 1.414 times the corresponding RMS value when waveforms are continuous sine or cosine. In an aspect, negative peak values may be calculated because the waveforms in discontinuous modes are not necessarily symmetric.

The digital signal processor 414 calculates the impedance by first calculating the RMS current and the average power as described above and then dividing the average power by the squared RMS current by using formulas (1) and (2), above.

The outputs (i.e., the voltage, the current, the power, and the impedance) of the digital signal processor 414 are stored in RF data registers 416 and provided to the software compensator 280 of FIG. 2 via the RF data registers 416. The DMAC 272 also includes DMAC registers 418 that receive and store relevant parameters for the digital signal processor 414. The digital signal processor 414 further receives signals from a PWM module 446 of the RF inverter controller 276. The RF data registers 416 may contain the RMS voltage $V_{rms}$, the RMS current $I_{rms}$, and the average power $P_{avg}$ or the peak voltage $V_{peak}$, and the peak current $I_{peak}$. The contents of the RF data registers 416 are also passed on to the software compensator 280. The DMAC registers 418 provide the interface between the digital signal processor 414 and the software compensator 280. The DMAC registers 418 provide setup information, including, but not limited to sensor comparison delta limits, high pass filter coefficients, sensor scale factors (e.g., calibration coefficients), and combinations thereof. The DMAC 272 provides fast path data to the hardware compensator 274 and slow path data to the software compensator 280. As described above, the slow path data takes more time than the fast path data but is closer to the actual value than the fast path data.

As shown in FIG. 2, the hardware compensator 274 processes the fast path data and outputs a control signal (e.g., a phase) to the RF inverter controller 276. With reference to FIG. 3, the hardware compensator 274 includes a setpointer 420, compensator registers 422, a compensator 424, impedance/high voltage (Z/HVDC) scheduler 426, an integrated error calculator 428, a Cphase scheduler 430, and a limiter 432. The setpointer 420 receives the fast path data (e.g., the RMS voltage, the RMS current, and the average power), determines whether the data corresponds to a target value, and also determines when to switch the target value among the RMS voltage, the RMS current, and the average power. Although only the RMS voltage, the RMS current, and the average power are described as target values, the target values may be any suitable set points, including, but not limited to, peak voltage, peak current, peak power, and combinations thereof.

The determinations are based on the measured values, e.g., RMS voltage, the RMS current, the average power, the desired values and maximum limits. Slow path data received from the software compensator 280 and default values may be stored in the compensator registers 422.

The setpointer 420 determines a switching time of the target when any control variable exceeds the corresponding maximum limit, and determines the control variable, which exceeds the corresponding maximum limit, as the target. In an aspect, the setpointer 420 may determine the switching timing and the target based on bumpless switch, meaning that change of the target does not cause a sudden change (i.e., a bump) in the output of the RF inverter 230. The setpointer 420 provides the target to the compensator 424.

The compensator 424 compensates the value of the target for electrical and logical components of the controller 260. The compensator 424 compares a value of the target with a desired value, which is received from the software compensator 280 or stored in the compensator registers 422, and uses the difference to update a phase $\varphi_3$ to the RF inverter controller 276. The compensator 424 may store and accumulate an integrated error term for the compensation. When setpointer 420 provides a new target, the compensator 424 resets the integrated error term. The compensator 424 runs once every RF waveform repetition, e.g., every RF cycle.

In an aspect, the compensator 424 implements a second order proportional/integral/differential (PID) compensation algorithm. In an aspect, the compensator 424 may implement a fixed point version of a discrete second order transfer function H(z) shown in formula (6) below:

$$H(z) = \frac{A_0 + A_1 \cdot z^{-1} + A_2 \cdot z^{-2}}{1 + B_1 \cdot z^{-1} + B_2 \cdot z^{-2}}, \quad (6)$$

where z is a discrete time variable, and $A_0$, $A_1$, $A_2$, $B_1$, and $B_2$ are constants, which can be obtained from a proportional constant, an integral constant, and a derivative constant of the PID compensation algorithm. By utilizing these implementations, the compensator 424 minimizes the difference (e.g., errors) between the measured value of the target provided by the DMAC 272 (i.e., RMS voltage, the RMS current, and the average power) and the desired value of the target set by the software compensator 280, and generates an output for adjusting the phase $\varphi_3$, which is the input to the RF inverter controller 276.

In an aspect, the compensator 424 operates once per every PWM period. The RF inverter controller 276 provides an update signal for compensation or a hold signal to the compensator 424. When the update signal indicates compensation, the compensator 424 performs compensation and, when the update signal indicates hold, the compensator 424 does not perform compensation.

In an embodiment, the compensator 424 may be a PID alpha controller, which contains a low pass filter on the derivative component of the PID controller. The PID alpha controller reduces sensitivity of the derivative term to high frequency noise. The PID controller may include a proportional constant $K_p$, an integral constant $K_i$, and a derivative constant $K_d$. The PID controller calculates an output based on the following formula (7):

$$\text{output} = K_p \cdot \text{Err} + K_i \cdot \text{IntErr} + K_d \cdot \text{dErr} \quad (7),$$

where Err is the difference or error between the measured value of the target value received from the setpointer 420 and the desired value of the target received from the software compensator 280, IntErr is an integrated error, and dErr is a derivative of the error. Specifically in the digital space, IntErr is calculated by the following formula (8):

$$\text{IntErr}_n = \text{IntErr}_{n-1} + \text{Err}_n \quad (8),$$

where $\text{IntErr}_n$ is the current integrated error, $\text{IntErr}_{n-1}$ is the previous integrated error, and $\text{Err}_n$ is the current error. Thus, IntErr is the sum of the current error and the previous integrated error.

The derivative of the error, dErr, is obtained by using the following formula (9):

$$\text{dErr}_n = \text{Err}_n - \text{Err}_{n-1} \quad (9)$$

where $\text{dErr}_n$ is the derivative of the current error, $\text{Err}_n$ is the current error, and $\text{Err}_{n-1}$ is the previous error. Thus, the derivative of the error is the difference between the current and previous errors.

In an aspect, the compensator 424 may include three separate PID compensator modules, one for each of the RMS voltage, the RMS current, and the average power. Since magnitudes for the RMS voltage, the RMS current, and the average power are different from each other, these three separate PID compensators are specifically designed to cover the corresponding ranges. In embodiments, the RMS voltage may be from about 1 to about 650volts, the RMS current may be from about 1 milli-Ampere to about 5.5 Amperes, and the average power may be from about 1 to about 375 watts.

The Z/HVDC scheduler 426 receives the measured impedance value and a high DC voltage value from the DMAC 272 and also receives a slow path impedance value from the software compensator 280. The Z/HVDC scheduler 426 generates an impedance-high voltage gain, ZHVDC gain, based on the impedance and the high DC voltage, which is the DC voltage provided by the preamplifier 225. ZHVDC gain may include two gain values, an impedance gain and a high-voltage gain. ZHVDC gain is designed to make the loop gain as constant as possible, since the RF inverter gain changes with both of the impedance and the HVDC values. The first phase $\varphi_1$ is obtained by multiplying the impedance-high voltage gain to the output of the compensator 424, as shown below:

$$\varphi_1 = (K_p \cdot \text{Err} + K_i \cdot \text{IntErr} + K_d \cdot \text{dErr}) \cdot \text{ZHVDC}_{gain} \quad (10).$$

In an aspect, voltage may change when a load (e.g., tissue to be treated) is coupled to the electrosurgical generator 102. When only the impedance gain is being processed by the compensator 424 and the voltage is the target value, the voltage varies based on the voltage divider rule and the resulted voltage gain due to the load may be calculated based on formula (11):

$$\frac{R_{Load}}{R_{Load} + |Z_0|}, \quad (11)$$

where $R_{Load}$ is impedance of the patient load and $|Z_0|$ is the magnitude of the matched load of the resonant tank 234. The impedance gain may be a reciprocal of the formula (11) so that multiplication of the formula (11) and the impedance gain is equal to one.

In another aspect, when the current is the target provided to the compensator 424, the current also changes when the load is loaded. The resulting current gain based on the load may be calculated using formula (12):

$$\frac{1}{R_{Load} + |Z_0|}. \quad (12)$$

Thus, the impedance gain may be a reciprocal of the formula (12).

In yet another aspect, when the average power is the target, the power also changes when the load is coupled to the electrosurgical generator 102. The resulting power gain due to the load may be calculated based on formula (13):

$$\frac{R_{Load}}{(R_{Load} + |Z_0|)^2}. \quad (13)$$

Thus, the impedance gain may be a reciprocal of the formula (13). In embodiments, the above-described gain formulas (11)-(13) may vary when another functional block (e.g., the Cphase scheduler 430 or the RF inverter 230) is considered and when a target is the RMS current or the average power.

In an aspect, when the high-voltage gain is considered, an inverter gain caused by the RF inverter 230 is expressed in the following formulas:

$$|V_{out}| = \frac{4V_g}{\pi} \sin\frac{\phi_s}{2} \cdot |H_v|, \quad (14)$$

$$|I_{out}| = \frac{4V_g}{\pi} \sin\frac{\phi_s}{2} \cdot \frac{|H_v|}{R_{load}}, \text{ and} \quad (15)$$

$$|P_{out}| = \frac{\left(\frac{4V_g}{\pi} \sin\frac{\phi_s}{2} \cdot |H_v|\right)^2}{R_{load}}, \quad (16)$$

where $H_v$ is a transfer function of the RF inverter 230, $|H_v|$ is the magnitude of the transfer function, or the high-voltage gain, $V_g$ is the magnitude of the voltage input to the RF inverter 230.

As shown in the formulas (14)-(16) for the high-voltage gain above, the output of the compensator 424 is linearly proportional to the high-voltage gain $|H_v|$ when the target is voltage or current, while the output of the compensator 424 is proportional to the square of the high-voltage gain $|H_v|$ when the target is average power.

In an aspect, the Z/HVDC scheduler 426 may include a lookup table for the ZHVDC gain. The lookup table contained in the Z/HVDC scheduler 426 may include a set of lookup tables for cases when the target is current, voltage, and average power. Methods of generating lookup tables are described in detail below with reference to FIGS. 6C-6F.

The output from the compensator 424 is multiplied by the ZHVDC gain to obtain the first phase $\varphi_1$. The Cphase scheduler 430 receives the first phase $\varphi_1$ and generates a phase gain. The first phase $\varphi_1$ is then multiplied by the phase gain, resulting in a second phase $\varphi_2$. The Cphase scheduler 430 may also include a lookup table, which may include a plurality of lookup tables, each of which is selected based on the type of the target value, e.g., current, voltage, or average power, respectively.

The limiter 432 receives the second phase $\varphi_2$ and checks whether the second phase $\varphi_2$ is within a desired range. If the second phase $\varphi_2$ exceeds the maximum of the desired range, then the limiter 432 outputs the maximum as the third phase $\varphi_3$, if the second phase $\varphi_2$ is lower than the minimum, the limiter 432 outputs the minimum, and if the second phase $\varphi_2$ is within the desired range, the second phase $\varphi_2$ is going to be the third phase $\varphi_3$, which is a phase shift value for the phase shift $\varphi_s$, to the RF inverter controller 276 and to the integrated error calculator 428.

Figure 5A:
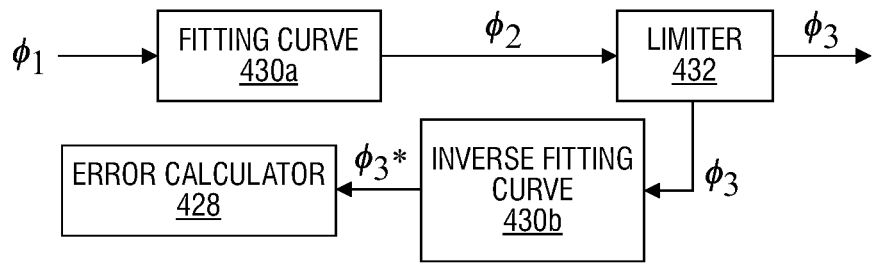
FIGS. 5A-5C are block diagrams of a phase gain scheduler of the electrosurgical generator of FIG. 2 in accordance with embodiments of the present disclosure.
Figure 5B:
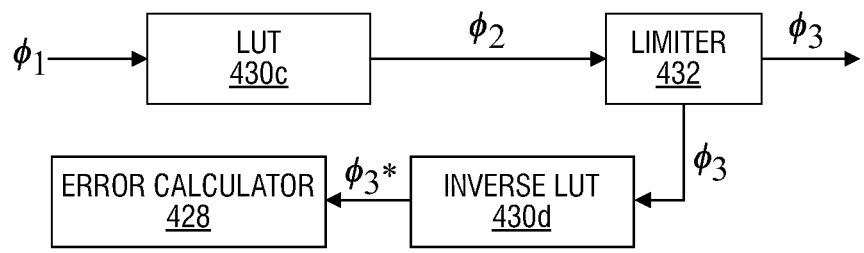
Figure 5C:
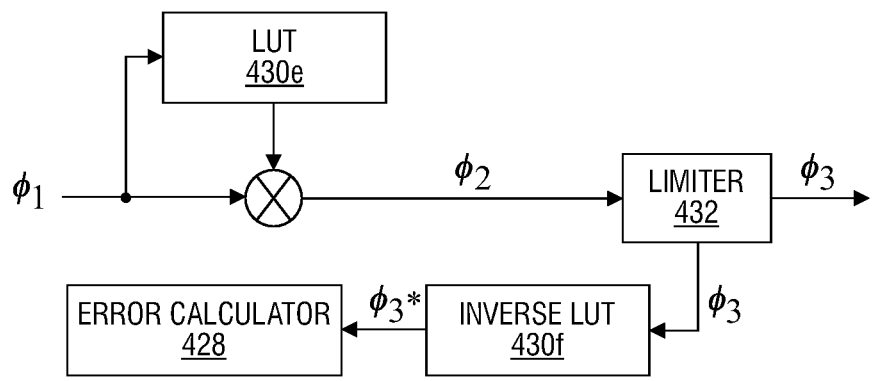

In embodiments, the Cphase scheduler 430 may be implemented in several ways as shown in FIGS. 5A-5C. FIG. 5A shows a polynomial method to calculate a phase input $\varphi_3$* to the integrated error calculator 428. The Cphase scheduler 430 includes a fitting curve block 430a and an inverse fitting curve block 430b. The fitting curve block 430a receives the first phase $\varphi_1$ and outputs the second phase $\varphi_2$ using a fitting curve, which may be a polynomial having the highest power N, which is greater than or equal to two, or a sum of trigonometric functions such as sine and cosine (e.g., Fourier summation). This fitting curve block 430a compensates the output of the RF inverter 230 so as to obtain the second phase $\varphi_2$. The limiter 432 outputs the third phase $\varphi_3$ as described above in FIG. 4. The third phase $\varphi_1$ is then provided to the inverse fitting curve block 430b which outputs the phase input $\varphi_3$* to the integrated error calculator 428. In as aspect, the fitting curve may be obtained by using a least square regression method.

In embodiments in which it may be difficult to find a function which is an inverse to the fitting curve used by the fitting curve block 430a, a lookup table (LUT) method may be used for the Cphase scheduler 430 as shown in FIG. 5B. The Cphase scheduler may include a LUT block 430c and an inverse LUT block 430d. A lookup table used in LUT block 430c and a lookup table used in inverse LUT block 430d are inverse to each other. The lookup tables may be obtained from using the fitting curve used in FIG. 5A or numerical analysis including linear interpolation. The LUT block 430c and the inverse LUT block 430d operates as same as the fitting curve block 430a and the inverse fitting curve block 430b.

FIG. 5C is another variation of using a lookup table method. In this method, a LUT block 430e generates a gain so that the first phase $\varphi_1$ is multiplied by the gain to obtain the second phase $\varphi_2$. And inverse LUT block 430f process the third phase $\varphi_3$ to provide the phase input $\varphi_3^*$ to the integrated error calculator 428.

The compensator 424 and the gains are to increase the phase shift $\varphi_s$ to compensate for changes in the control system loop gain due to effects of the load, HVDC, and the non-linear nature of the inverter output. This attempts to keep the control system response as consistent as possible over the operating range of the control system.

When the phase shift $\varphi_s$ hits the minimum or maximum limit, the integrator increases or winds up. If the increase of the integrator is used, it causes a bump or jump in the control system output, which is undesirable because the integrated error has to be unwound before the computed phase shift falls between the minimum and the maximum limits. In this instance, the integrated error calculator 428 receives the first, second, and third phases, $\varphi_1$, $\varphi_2$, and $\varphi_3$, the impedance gain, the high voltage gain, and the phase gain, and recalculates an integrated error for the compensator 424 such that changes caused by the gains (e.g., the impedance gain, the high voltage gain, and the phase gain) and the PID parameters of the compensator 424 do not result in a phase shift that is less than the minimum limit or greater than the maximum limit.

When the phase shift is less than the minimum limit or greater than the maximum limit, the integrated error is recalculated to achieve a phase shift within the minimum limit and the maximum limit. Further, when the ZHVDC gain changes, or when inputs from the setpointer 420 changes due to a control mode change (e.g., from current control mode to voltage control mode or to the power control mode), the integrated error is recalculated. In embodiments, when the integrated error is to be recalculated, the new integrated error can be calculated using formula (17):

$$IntErr_n = \frac{\frac{\phi_1}{ZHVDC_{gain}} - K_{p\_n} \cdot Err_n}{K_{i\_n}}, \quad (17)$$

where subscript "n" represents a temporal current state, meaning that $K_{p\_n}$ is the current proportional constant, $K_{i\_n}$ is the current integral constant, and $IntErr_n$ is the current integrated error and "n+1" represents a next state, meaning that $IntErr_{n+1}$ is the next integrated error.

In an aspect, the integrated error calculator 428 may be used when the second phase $\varphi_2$ is limited by the limiter 432 so that the integrated error does not windup during operations of the limiter 432. In other words, when the second phase $\varphi_2$ is limited by the limiter 432, the integrated error is increased as the compensator 424 attempts to raise the output past the limit. If the target is changed, conditions are changed, or the second phase $\varphi_2$ is limited by the limiter 432, the compensator 424 may create an undesirable change in the output due to the integrated error stored in the compensator 424. Thus, in these situations, the integrated error stored in the compensator 424 needs to be removed or updated. The integrated error calculator 428 recalculates the integrated error so that the compensator 424 can generate an output with this recalculated integrated error. In this way, wind-up occurrences may be prevented. This also prevents wind-up occurrences in cases when the target changes, parameters of the PID controller change, or the ZHVDC and phase gains change.

As to the phase gain calculation, the following formulas may be used:

$$|V_{out}| = \frac{4V_g}{\pi}\sin\frac{\phi_s}{2} \cdot |H_v|, \quad (18)$$

$$|I_{out}| = \frac{4V_g}{\pi}\sin\frac{\phi_s}{2} \cdot \frac{|H_v|}{R_{load}}, \text{ and} \quad (19)$$

$$|P_{out}| = \frac{\left(\frac{4V_g}{\pi}\sin\frac{\phi_s}{2} \cdot |H_v|\right)^2}{R_{load}}. \quad (20)$$

The phase gain comes from the term, $$\sin\frac{\phi_s}{2}.$$

Figure 6A:
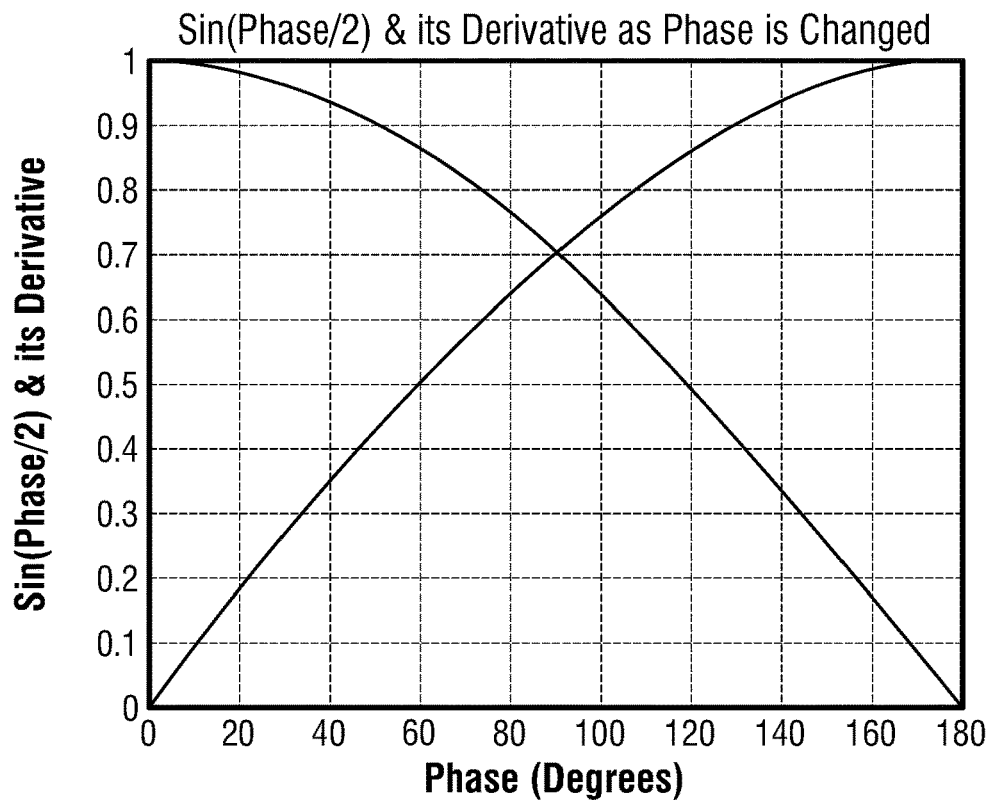
FIGS. 6A and 6B are phase gain plots in accordance with embodiments of the present disclosure.
Figure 6B:
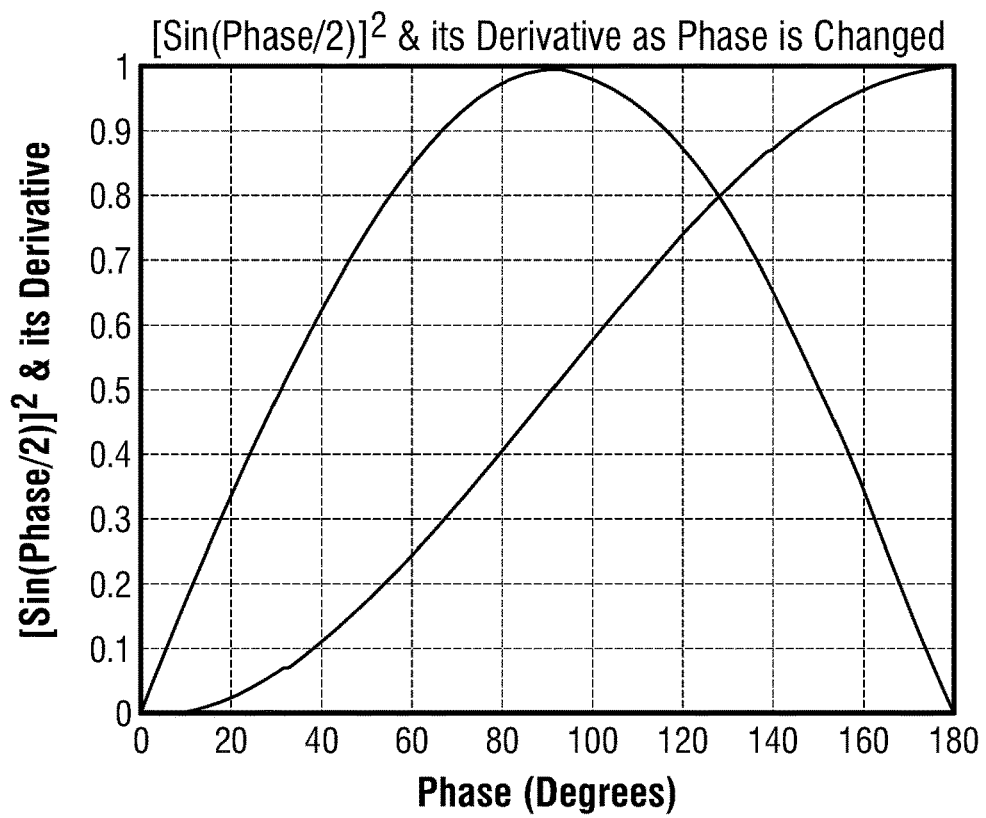

As shown in the above formulas (18)-(20), the phase gain of the voltage and current is $$\sin\frac{\phi_s}{2},$$

which is shown in FIG. 6A and the phase gain of the average power is the square of $$\sin\frac{\phi_s}{2},$$

which is shown in FIG. 6B.

FIG. 6A shows a graph of $$\sin\frac{\phi_s}{2}$$

starting from the origin point, and a graph of its derivative starting from 1 in the vertical axis, where the phase shift $\varphi_s$ ranges from 0 degree to 180 degrees. The horizontal axis represents a phase and the vertical axis represents magnitude of $$\sin\frac{\phi_s}{2}$$

or its derivative. Note that the derivative of $$\sin\frac{\phi_s}{2} \text{ is } \frac{1}{2}\cos\frac{\phi_s}{2}$$

and thus the maximum magnitude of the derivative is $$\frac{1}{2}.$$

Here, the maximum magnitude of the derivative is normalized to one as shown in FIG. 6A. FIG. 6B shows a graph of the square of $$\sin\frac{\phi_s}{2}$$

having a quarter sine wave and a graph of its derivative having a half sine wave.

Figure 6C:
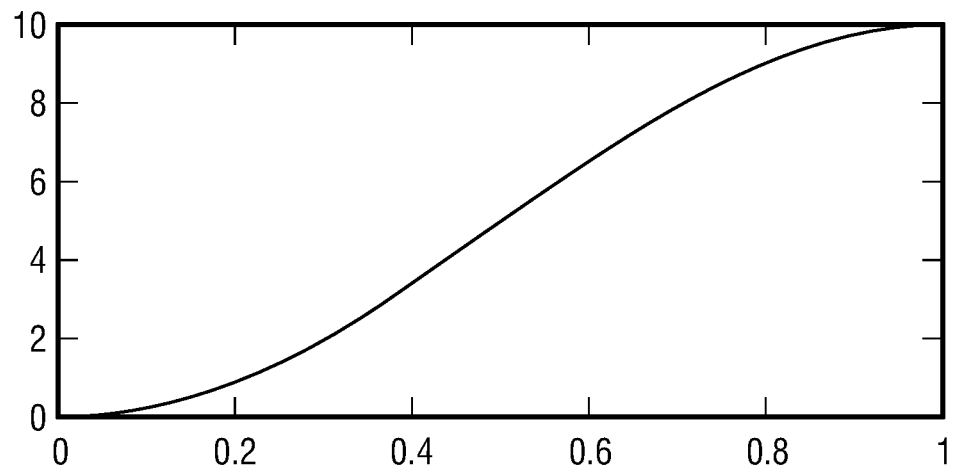
FIGS. 6C-6F are plots of a method to calculate a lookup table for a phase gain stored in a gain scheduler of the electrosurgical generator of FIG. 2 in accordance with embodiments of the present disclosure.

FIGS. 6C-6F illustrate a method to calculate a lookup table for a phase gain when the target is the average power. This method can be applied to calculate lookup tables for the impedance gain and the HVDC gain. FIG. 6C shows power variations caused by the RF inverter 230 with respect to the phase. The horizontal axis represents a phase difference, which is normalized to one, and the vertical axis represents a power difference. The phase gain is calculated by dividing the difference of the output of the RF inverter 230 by the difference of the phase shift. Thus, the gain caused by the RF inverter 230 can be obtained from the graph of FIG. 6C.

Figure 6D:
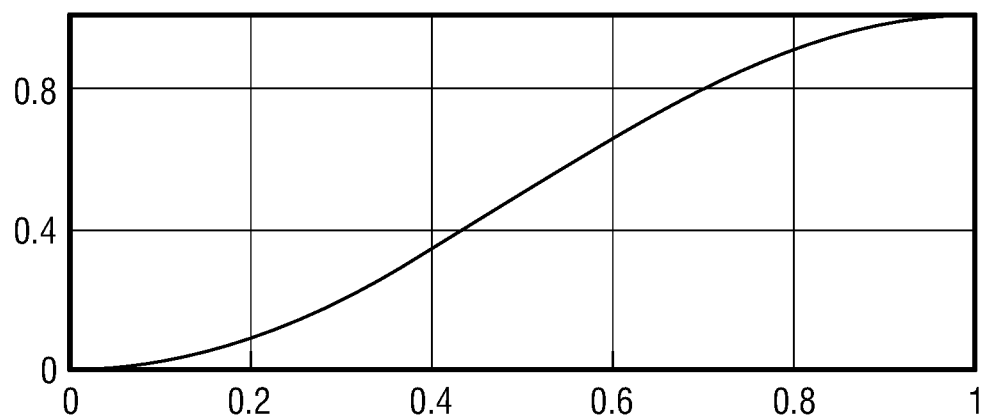
Figure 6E:
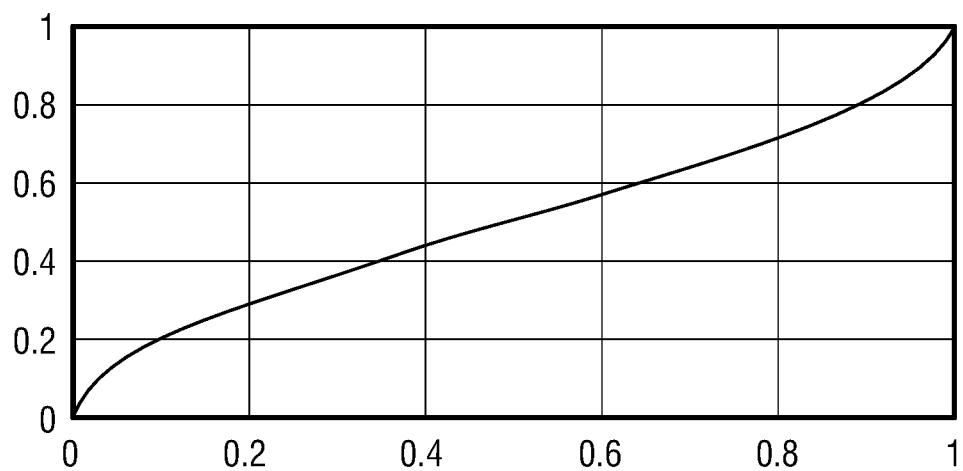
Figure 6F:
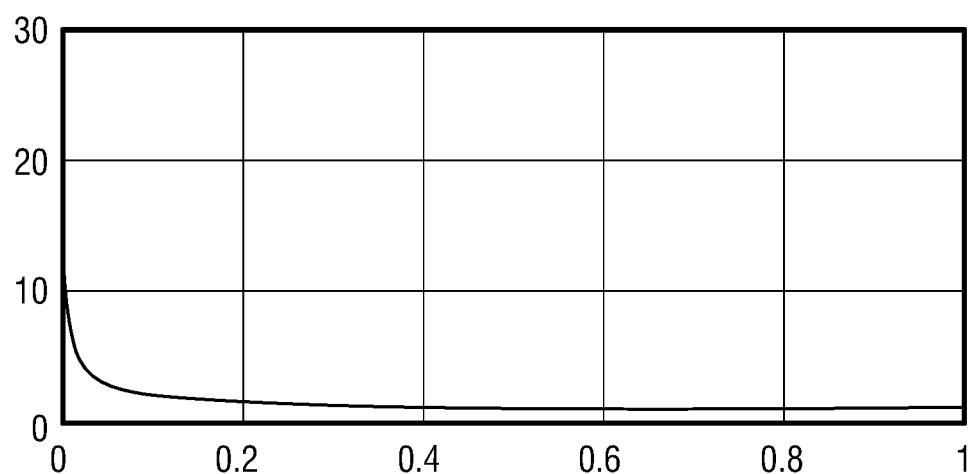

In order to calculate a lookup table contained in the Cphase scheduler 430, the magnitude of the gain is normalized to one as shown in FIG. 6D. The horizontal axis and the vertical axis of FIG. 6D are swapped as shown in FIG. 6E. FIG. 6F shows a graph whose values in the vertical axis are obtained by dividing values in the vertical axis of the graph of FIG. 6E by the normalized phase ranging from zero to one. The lookup table has two columns, the first column represents the phase shift, which is the second phase $\varphi_3$, and the second column is for the phase gain. Thus, a value in the horizontal axis is a value in the first column of the lookup table and the corresponding value in the vertical axis is the corresponding value in the second column of the lookup table.

When the hardware compensator 274 outputs the third phase $\varphi_3$ as a phase shift value, the RF inverter controller 276 processes the third phase $\varphi_3$ and outputs control signals for the phase-shift PWM signal to control the RF inverter 230. The control signal is generated for each PWM period. The RF inverter controller 276 can also control the compensation of the compensator 424 for each PWM period by providing a hold/compensate control signal to the hardware compensator 274. In this way, the RF inverter controller 276 may update the third phase $\varphi_3$, as a phase shift value for the phase shift $\varphi_s$ for calculating variables for PWM signal.

With reference to FIG. 4, the RF inverter controller 276 includes a scale 442, PWM registers 444, and a PWM module 446. The scale 442 receives the third phase $\varphi_3$ and scales it to a value that is appropriate for PWM variable, which may be a signal falling time related to pulse width compensation, a Bphase or Cphase related to the phase shift compensation, or a period value related to frequency compensation. In embodiments, the PWM variable may be a Bphase or Cphase. The scale 442 may implement a linear formula (21) as follows:

$$\varphi_s = M^*(\varphi + \varphi_3) + B \quad (21),$$

where M is a scalar coefficient, $\varphi$ is a phase, $\varphi_3$ is a phase shift, and B is a constant. The phase is scaled for PWM signals. In other words, the phase is converted to a temporal delay for the PWM module 446.

The PWM registers 444 may include four registers storing parameters, a PWM period, a pulse width, and a phase. Values stored in the four registers may be updated or replaced with new values, such as the scaled third phase and the desired values for RMS voltage, current, and power from the software compensator 280. The PWM registers 444 provides the updated or renewed values to the PWM module 446.

Upon reception of the values from the PWM registers 444, the PWM module 446 provides control signals to the RF inverter 230. The control signal is for a phase-shifted PWM signal. The PWM module 446 further provides the hold/compensate signal to the compensator 424 of the hardware compensator 274 so that the PWM module 446 can control the compensator 424 when to compensate and when to hold.

Figure 7:
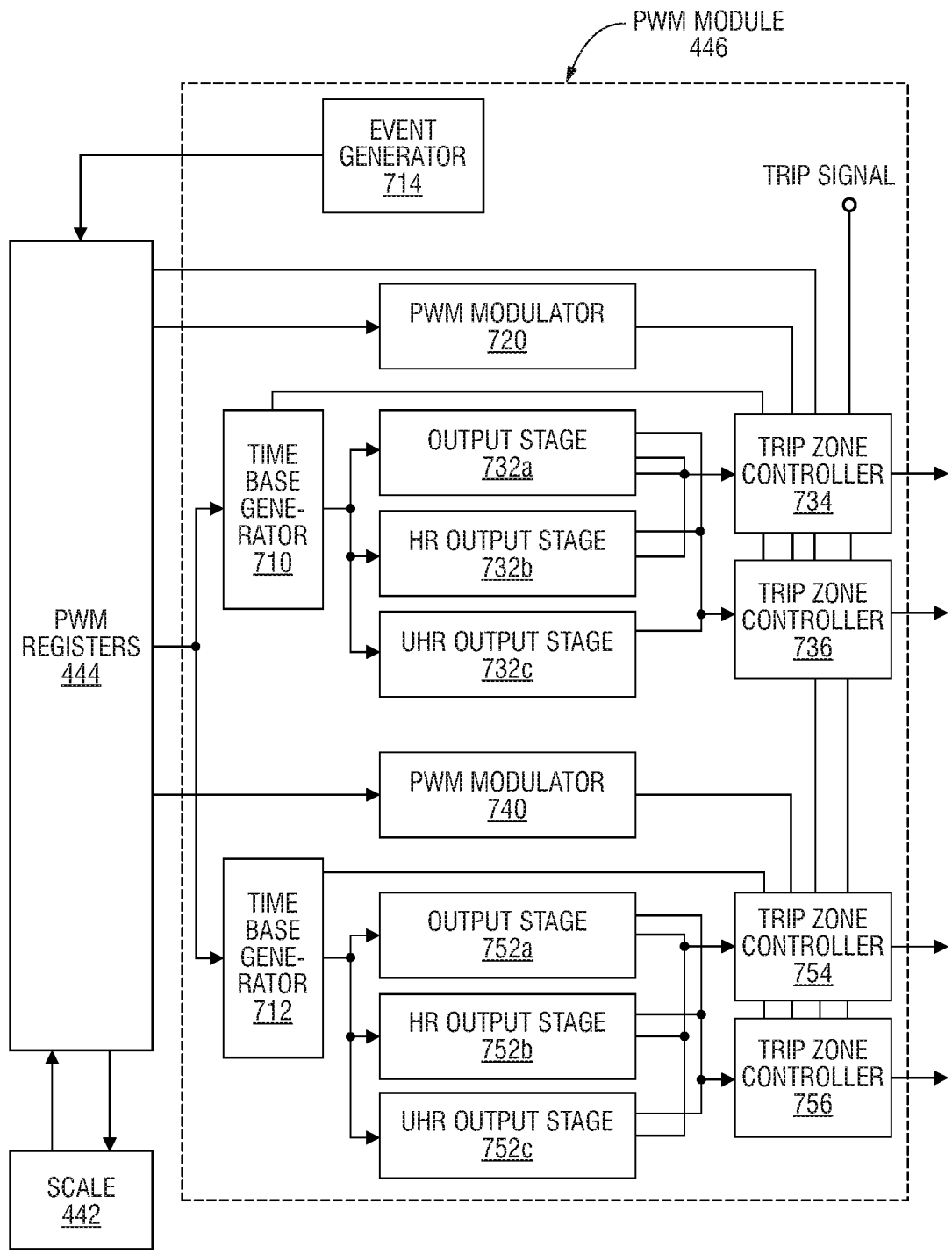
FIG. 7 is a functional block diagram of a PWM module of the electrosurgical generator of FIG. 2 in accordance with embodiments of the present disclosure.

FIG. 7 shows an embodiment of the PWM module 446 of FIG. 4 that may be capable of providing different resolutions with respect to the period, pulse width, and phase relationships. The PWM module 446 includes time base generators 710 and 712, an event generator 714, PWM modulators 720 and 740, output stages 732a and 752a, high resolution (HR) output stages 732b and 752b, ultra high resolution (UHR) output stages 732c and 752c, and trip zone controllers 734, 736, 754, and 756.

The time base generators 710 and 712 directly manage frequency, duty cycle, rising and falling edge delays, and phase shifts. Each time base generator 710 or 712 further manages two control signals among the control signals to the RF inverter 230, respectively, and provides information necessary for generating output signals with multiple levels of resolutions. In an aspect, when the clock of the time base generator generates 125 megahertz (MHz) clock signals, the time base generator can generate 8 nanosecond (ns) of resolution.

In embodiments, the time base generators 710 and 712 may generate three different clock signals for the output stages, the HR output stages, and the UHR output stages. The number of output stages is not limited to three but can be expanded to more than three. In an aspect, when the time base generator operates at 125 MHz, the output stages 732a and 752a may also operate at 125 MHz clock signals or 8 ns of resolution, the HR output stages 732b and 752b may operate at 1 gigahertz (GHz) clock signals or 1 ns of resolution. In another aspect, the time base generator 710 or 712 may operate at a faster clock signal so that the UHR output stage 732c and 752c may operate at 12.5 GHz clock signals or 80 picosecond (ps) of resolution.

The event generator 714 generates periodic synchronization signals. In an aspect, the event generator 714 may generate event signals at programmable offsets within the period of clock signal of the time base generator 710 or 712. In other words, multiple event signals may be generated within a period of the clock signal of the time base generator. For example, when the time base generators 710 and 712 operate at 125 MHz clock signals, the period of the clock signals is 8 ns and the event generator 714 generates multiple event signals within 8 ns. In another aspect, the multiple event signals may be equally spaced within the period of the clock signal.

Additionally, the event generator 714 may generate one event signal every N periods of the clock signal and the event signal may last for M periods, where N and M are natural numbers and M is less than N.

Output stages, 732a and 752a, generate output signals within a predetermined period or resolution and provide the output signals to the trip zone controllers 734 and 754, respectively. In the same manner, the HR output stages 732b and 752b and the UHR output stages 732c and 752c also generate and provide output signals to the corresponding trip zone controllers 736 and 756.

The trip zone controllers 734, 736, 754, and 756 are the final circuit to generate the control signals for the phase-shifted PWM to the RF inverter 230. The trip zone controllers 734, 736, 754, and 756 receive a trip signal and parameters from the PWM registers 444. The trip zone controllers 734, 736, 754, and 756 may be tripped or held in an inactive state based on the trip signal. In other words, when a trip signal to any one of the trip zone controllers 734, 736, 754, and 756 is active, then the corresponding trip zone controller 734, 736, 754, or 756 is being held inactive and when the trip signals to all of the trip zone controllers 734, 736, 754, and 756 are inactive, then all of the trip zone controllers 734, 736, 754, and 756 output control signals. The trip zone controllers 734, 736, 754, and 756 are set active when a measured parameter (e.g., the RMS voltage, the RMS current, or the average power), which is external to the PWM module 446, exceeds a critical level. Since inactive state of only one trip zone controller 734, 736, 754, or 756 can disable the control signal for the phase-shifted PWM signal, the RF inverter 230 is turned off quickly and is prevented from malfunctions or failures.

In an aspect, the trip zone controllers 734, 736, 754, and 756 may be also set active when signals internals to the RF inverter 230 exceed a critical level. This feature can protect hardware components from hardware failures.

In embodiments, the PWM registers 444 receives parameters from the software compensator 280 for adjusting values stored in the PWM registers 444. The software compensator 280 may consistently adjust threshold values for the trip zone controllers as the impedance of the load decreases or increases. The threshold values may be based on the RMS values or the peak values for the voltage, current, and average power.

In an aspect, the trip zone controllers 734, 736, 754, and 756 may include a leading-edge blanking feature, meaning that the trip zone controllers can ignore the trip signal at the beginning of each PWM period. After the leading-edge blanking period is over, the trip signal is resumed to be enabled, meaning that a trip signal within the leading-edge blanking period cannot make a trip zone controller inactive, but a trip signal outside of the leading-edge blanking period can make a trip zone controller inactive. Even when all of the trip zone controllers 734, 736, 754, and 756 may be tripped or inactive by the trip signal, the control signals of the PWM module 446 are always driven and never tri-stated. In other words, trip zone controllers 734, 736, 754, and 756 may generate control signal having a constant output when one of the trip zone controllers 734, 736, 754, and 756 is inactive so that the RF inverter 230 cannot generate AC signals.

The trip signal may be a cycle-by-cycle trip event, a multi-cycle trip event, or a trip-hold event. The cycle-by-cycle trip event may cause the control signals, which are output from the PWM module 446, to be held in its inactive state until the end of the current period of the clock signals of the time base generator 710 or 712. At each period of the clock signal, the trip signal may be automatically enabled.

The multi-cycle trip event may cause the control signals to be held in its inactive state for a number of periods of the clock signal. After the number of periods, the trip signal may be automatically enabled.

The trip-hold event may cause the control signals to be held in their inactive states indefinitely. This inactive state may be made by external inputs. As described above, inactive state of a trip zone does not mean that the corresponding trip zone controller does not generate a control signal. That means that the corresponding trip zone controller outputs a constant or consistent control signal with which the RF inverter 230 cannot generate AC signals.

The PWM modulators 720 and 740 may be used to modulate the control signals output from the PWM module 446 so that the control signals are enabled for M of N periods of the time base generator. That is the control signals are modulated only for the first M periods during the N periods. Thus, modulation of the control signals for the last N-M periods may be disabled. This feature is related to the leading-edge blanking period feature described above in the trip zone controllers. In other words, while modulation of the control signals are enabled, the trip signals are disable for the first M periods during the N periods.

In embodiments, control variable may be set to one among the voltage, current, and power rather than switching them based on values for the voltage, current, and power. This system is called a multi-input single output (MISO) control system. Since the target variable is set, there is no need to determining which variable is set to be a target variable and when to switch the target variable. For example, when the target variable is the voltage, whether it is the RMS or peak voltage, the hardware compensator 274 only compensates the voltage for the phase shift.

Figure 8A:
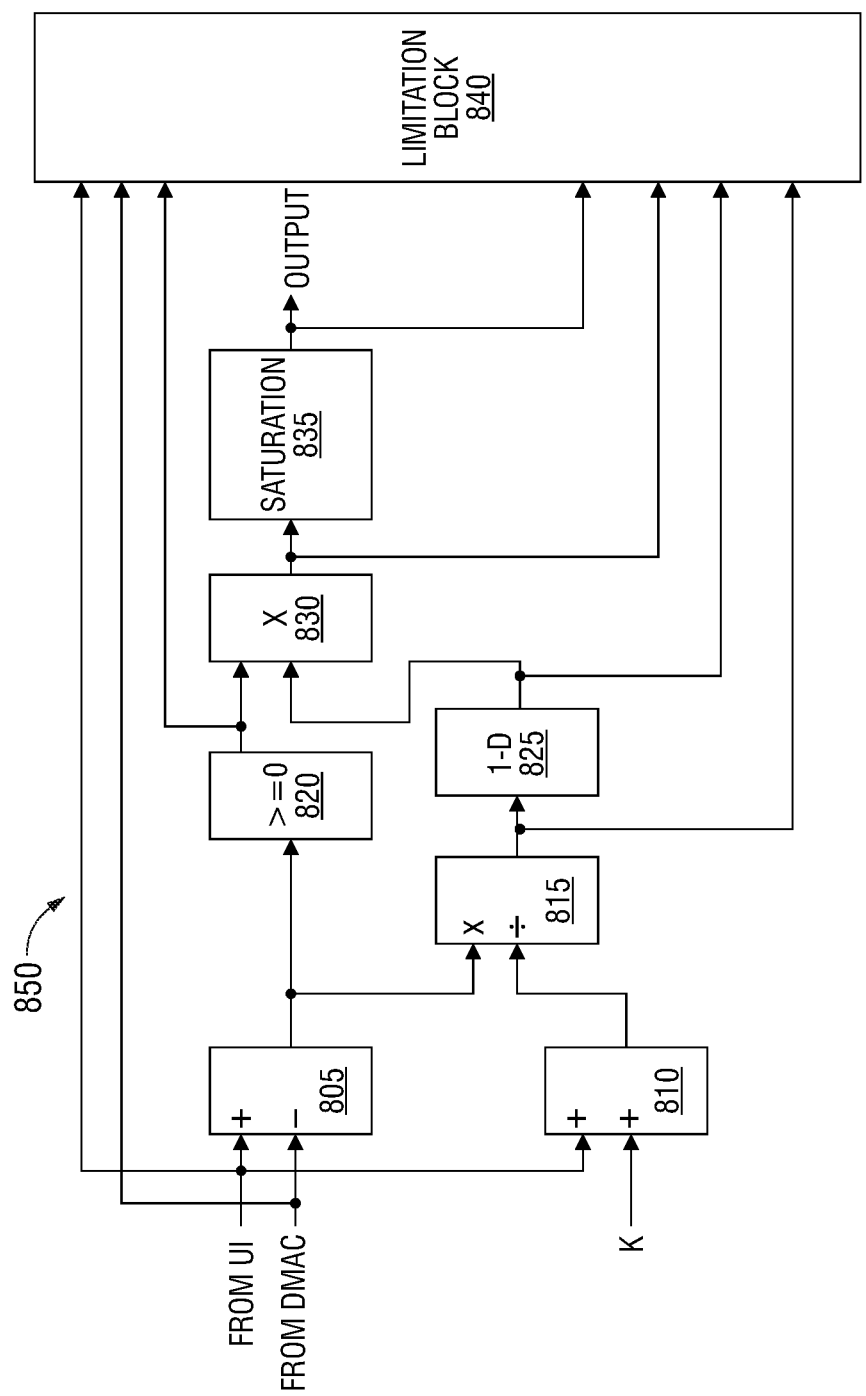
FIGS. 8A and 8B are functional block diagrams of a controller of the electrosurgical generator of FIG. 2 in accordance with embodiments of the present disclosure.
Figure 8B:
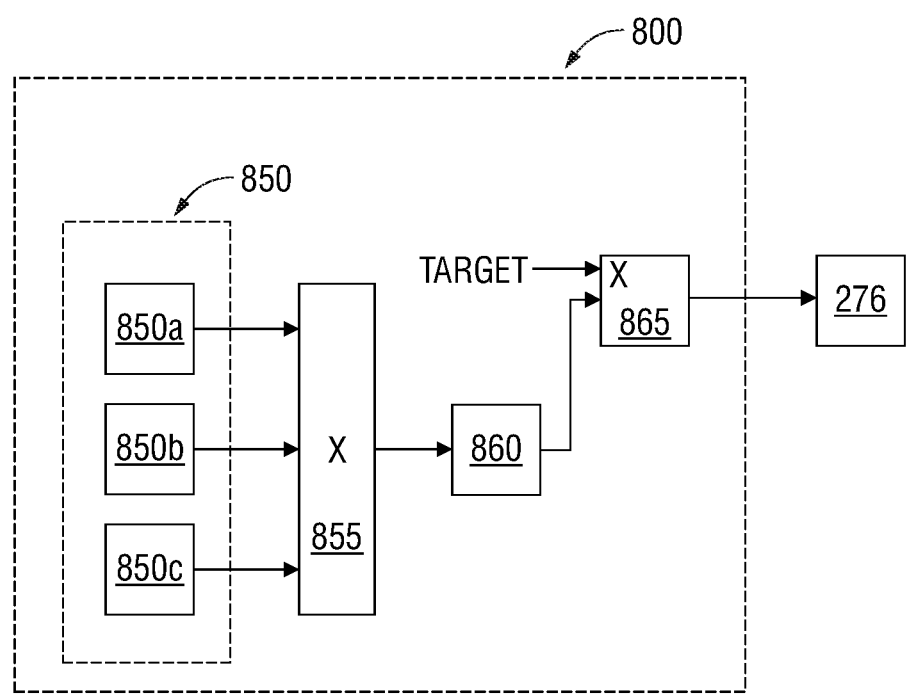

FIGS. 8A and 8B show block diagrams of the MISO control system, which may replace the software compensator 280 and the hardware compensator 274 of the electrosurgical generator 200 of FIG. 2. A software compensator 850 of the MISO control system receives data from the UI 290 and the DMAC 272. The data from the UI 290 is desired limits for the RMS voltage, the RMS current, and the average power and the data from the DMAC 272 is measured values for the RMS voltage, the RMS current, and the average power. The desired limits may be obtained from a table stored in the software compensator 850 based on the measured values from the DMAC 272. Results of the software compensator 850 of the MISO control system are a pulse train with a range from 0 to 1.

Subtraction block 805 subtracts a measured value from a desired limit and provides an output from the subtraction to a comparison block 820. If the measured value is greater than or equal to the desired limit, the comparison block 820 outputs zero, and if not, the comparison block 820 outputs one.

Addition block 810 adds a constant value to the desired limits so that an error of division by zero is prevented. The constant value may be a very small number compared to the desired limits. Division block 815 then divides the output of the subtraction block 805 by the output of the addition block 810 and calculates a percentage difference between the actual value and the desired limit. In an aspect, the software compensator 850 may include separate subtraction block and separate addition block for each of the voltage, current, and the power.

The output of the comparison block 820 goes from zero to one when the measured value becomes less than the desired limit and provides the result to 1-D LUT 825, which includes a LUT by calculating percentage differences between the desired limit and the measured value based on formula (22):

$$\text{Percentage difference} = \frac{\text{desired value} - \text{measured value}}{\text{desired value}}. \quad (22)$$

The 1-D LUT 825 control to generate a very small value when the desired value is close to the measured value and generally a value smaller than one.

When two output values are multiplied by multiplication block 830, the result can be smaller than the measured value because of the LUT stored in the 1-D LUT 825. The saturation block 835 then saturates the output from the multiplication block 830 to limit the output to be within a predetermined range.

The limitation block 840 receives inputs from the UI 290, the DMAC 272, the division block 815, the comparison block 820, the 1-D LUT 825, the multiplication block 830, and the saturation block 835 and outputs a pulse train. The pulse train has a minimum of zero when the actual value is greater than the desired limit, has a value between zero and one when the actual value is close to the desired limit, and has a maximum of one when the actual value and the desired limit are far apart. Thus, the pulse train of the limitation block 840 is used to allow a gentle adjustment and less ripple or bump is resulted when the actual value is bouncing around the desired limit. In other words, when the voltage, current, or power is greater than the corresponding desired limit, the output is close to zero, and when any one is far less than the desired limit, the output is close to one.

FIG. 8B shows a block diagram of the MISO control system 800. The MISO control system 800 includes the software compensator 850, a multiplication block 855, a filter 860, and a multiplication block 865. The software compensator 850 includes three blocks 850*a*-850*c*, each of which includes all the components in FIG. 8A and outputs a value based on the voltage, current, and power, respectively. The multiplication block 855 multiplies the three outputs from the software compensator 850 and provides its result to the filter 860. In an aspect, the multiplication block 855 may also collect other limits such as crest factor, peak values, etc. Since the result of the software compensator 850 is the output of each limitation block 840, the result of the software compensator 850 is ranged from zero to one. Thus, the result of the multiplication block 855 is also ranged from zero to one is at least less than or equal to each of the outputs of the limitation blocks 840.

The filter 860 may be a first order low pass filter or a higher order low pass filter. The higher the order is, the slower the response is. On the other hand, the lower the order is, the higher the ripple in the response is. The filter 860 removes higher frequency portions or noise in the output from the multiplication block 855. The multiplication block 865 then multiplies the output from the filter 860 to the measured value of the target which is predetermined among the voltage, current, and the power. The output of the multiplication block 865 is then input to the RF inverter control 276. In a case when any measured value of the voltage, current, and power exceeds the corresponding desired limit, the output of the filter 860 is less than 1.0. Thus, when multiplied by the output of the filter 860, the output of the MISO control system 800 becomes less than the target and thus less than the corresponding desired limit. In a case when no measured values are greater than the desired limit, the output of the filter 860 is equal to 1.0 and when multiplied by the output of the filter 860, the output of the MISO control system 800 is equal to the target and thus less than the corresponding desired limit. In this way, the output value of the MISO control system 800 may remain within a desired range. In an aspect, implementation of the MISO control system 800 is structurally simpler than the implementation of the hardware compensator 274 of FIG. 4.

Figure 9:
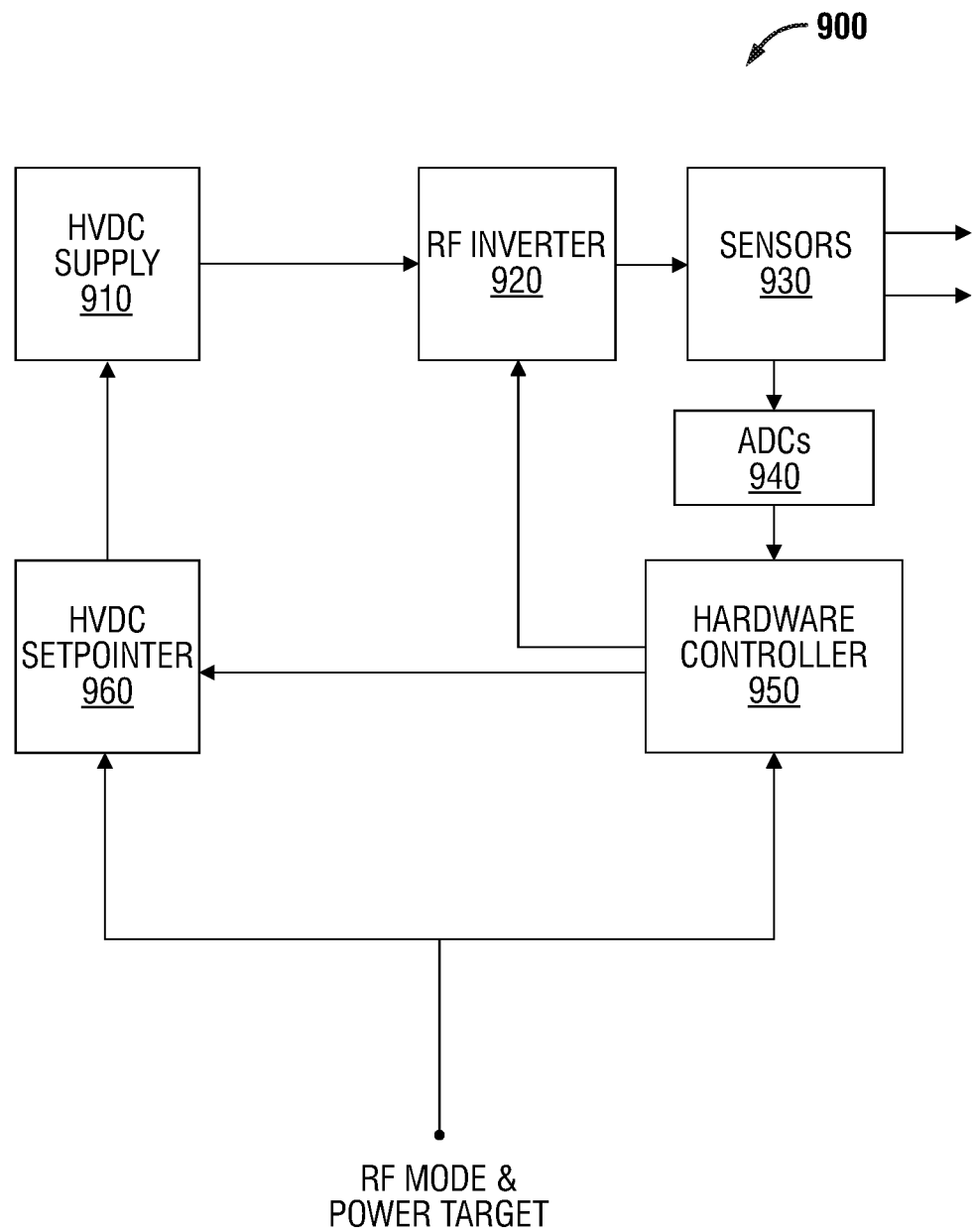
FIG. 9 is a block diagram of the electrosurgical generator of FIG. 2 in accordance with embodiments of the present disclosure.

FIG. 9 illustrates another control system for the electrosurgical generator 102 of FIG. 1. This simplified block diagram shows an electrosurgical generator 900 having a high voltage DC power control scheme. The electrosurgical generator 900 includes a high voltage DC (HVDC) power supply 910, an RF inverter 920, sensor 930, ADCs 940, hardware controller 950, and a HVDC setpointer 960. The HVDC power supply 910 provides a high voltage DC power to the RF inverter 920. A value for the HVDC power is set by the HVDC setpointer 960.

The RF inverter 920, the sensors 930, and the ADCs 940 operate similarly as the RF inverter 230, the sensors 240, and the ADCs 250 of FIG. 2. Thus, the descriptions of them are omitted.

As described above in FIG. 3B, the input voltage to the resonant tank of the RF inverter is a square wave. Fourier series approximation of the square wave is following:

$$\sum_{n=1,3,5,\ldots}^{\infty} \frac{4HVDC}{n\pi} \sin\left(\frac{n\phi_{12}}{2}\right) \cos(n\omega_s t), \qquad (23)$$

where HVDC is the magnitude of the square wave, $\phi_{12}$ is a phase of the PWM signal, and $\omega_s$ is the switching frequency of the RF inverter. As shown in the formula (23), RF waveform is distorted based on the phase $\phi_{12}$. This is due to the high frequency harmonic content of the square wave. Significant contents of the harmonics are in the third and fifth harmonics.

Figure 10:
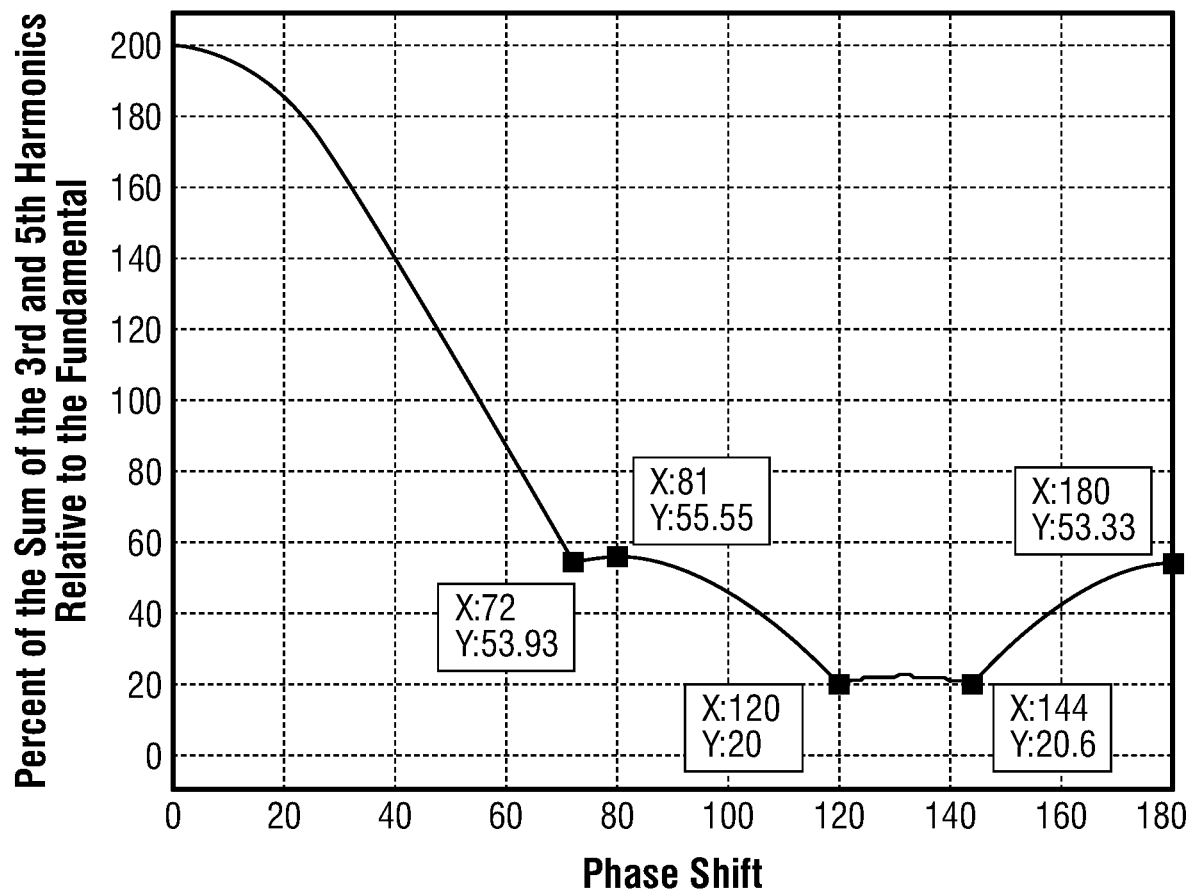
FIG. 10 is a plot of percentage contribution of the third and fifth harmonics relative to the fundamental of the PWM signal.

FIG. 10 shows a graph of contribution of the third and fifth harmonics relative to the fundamental of the PWM signal input to the resonant tank of the RF inverter 920. The vertical axis represents percent of the sum of the third and fifth harmonics and the horizontal axis represent a phase ranging from 0 to 180 degrees. The graph shows several local maximums and minimums. It is apparent that the contribution of the third and fifth harmonics is minimal over a range of phases from 120 to 144 degrees.

Amplitude of the Fourier components of the square wave of formula (23) is determined by the product of the HVDC and the phase. Thus, by raising the HVDC, the electrosurgical generator 900 needs a lower phase to reach the same output it would get by lowering the HVDC and increasing the phase. HVDC term is a direct multiplier to the Fourier component, while the phase term is an indirect multiplier, which is in the form of sine, to the Fourier term. Thus, controlling the HVDC term will result in linear control of the output of the RF inverter 920.

The RF inverter 920 tends to run more efficiently within a certain range of phase. For example, as the phase increases, an H-bridge in the RF inverter 920 transitions from hard switching, which is inefficient, to zero voltage switching (ZVS), which is very efficient. During this transition, the output of the RF inverter 920 changes little with a change in the phase.

Further, changes of the phase result in different changes in the output of the RF inverter 920 depending on the value of the phase, meaning non-linear changes. Thus, by controlling the HVDC term and keeping the phase constant, the control system of the electrosurgical generator 900 is simplified.

The hardware controller 950 receives digital samples of the voltage and current waveforms and a desired value for the voltage and current, and controls the RF inverter 920 by selecting an ideal PWM phase which is near the range where the contribution of the third and fifth harmonics are minimal or where the H-bridge of the RF inverter 920 operates in ZVS, and controls the HVDC to control the output of the RF inverter 920. The hardware controller 950 also provides a measured power to the HVDC setpointer 960.

The HVDC setpointer 960 receives the measured power and a desired power, and compares the difference between them. The HVDC setpointer 960 sets and provides a magnitude to the HVDC power supply 910, which generates the corresponding power having the magnitude, accordingly.

By controlling the HVDC and fixing the phase, this controlling system minimizes harmonic distortion in the output of the RF inverter 920, minimizes RF high frequency leakage, minimizes heat dissipation by keeping the RF inverter 920 in an efficient range, increases this controlling system performance by keeping the change of the output of the RF inverter 920 in its linear range, increases the energy output ranges of the RF inverter by allowing changes in the HVDC during activation of the electrosurgical generator 900, and adjusts any inaccuracies in the HVDC output.

In other words, the HVDC setpointer 960 controls the HVDC term much more slowly than the hardware controller 950 controls the phase. In particular, the hardware controller 950 updates the phase relatively quickly but the updated phase is less accurate, while the HVDC setpointer 960 controls and keeps the HVDC term within a preferred range relatively slowly but the HVDC term is more accurate.

In an aspect, when the electrosurgical generator 900 is activated, the HVDC level is set to a default by the HVDC setpointer 960. The hardware controller 950 receives digital data from the sensors 930 via the ADCs 940 and calculates a phase shift. Further, the hardware controller 950 compares the phase with a desired threshold, which may be the fixed phase used by the RF inverter 920.

When the phase is greater than the desired threshold, the HVDC setpointer 960 increases the value for the HVDC power so that the HVDC supply 910 generates higher DC power. When the phase is less than the desired threshold, the HVDC setpointer 960 decreases the value for the HVDC power so that the HVDC supply 910 generates lower DC power. In this way, the level of the HVDC power is set within a desired range or sufficiently equal to the desired threshold.

Although the illustrative embodiments of the present disclosure have been described herein with reference to the accompanying drawings, it is to be understood that the disclosure is not limited to those precise embodiments, and that various other changes and modification may be effected therein by one skilled in the art without departing from the scope or spirit of the disclosure.

What is claimed is:

1. A controller for an electrosurgical generator, the controller comprising:
    a radio frequency (RF) inverter including an H-bridge configured to generate a first electrosurgical waveform from a first pair of switches of the H-bridge and a second electrosurgical waveform from a second pair of switches of the H-bridge;
    a signal processor configured to output a measured value of at least one of a voltage, a current, or a power of the first and second electrosurgical waveforms;
    a software compensator configured to generate a desired value for at least one of the voltage, the current, or the power of the first and second electrosurgical waveforms;
    a hardware compensator configured to generate a phase shift between the first and second electrosurgical waveforms based on the measured value and the desired value; and
    an RF inverter controller configured to generate a pulse-width modulation (PWM) signal based on the phase shift to control the RF inverter.

2. The controller according to claim 1, wherein the hardware compensator includes:
    a setpointer configured to select a target value for at least one of the voltage, the current, or the power of the first and second electrosurgical waveforms; and
    a compensator configured to compensate for a first phase based on the target value.

3. The controller according to claim 2, wherein the compensator includes a proportional-integral-differential (PID) controller.

4. The controller according to claim 3, wherein the PID controller implements a second order PID algorithm.

5. The controller according to claim 2, wherein the software compensator and the hardware compensator perform compensation for each period of the PWM signal.

6. The controller according to claim 2, wherein the hardware compensator further includes:
    an impedance gain scheduler configured to calculate an impedance gain;
    a voltage gain scheduler configured to calculate a voltage gain; and
    a phase gain scheduler configured to calculate a phase gain.

7. The controller according to claim 6, wherein the hardware compensator is further configured to multiply the first phase by the impedance gain and the voltage gain to obtain a second phase.

8. The controller according to claim 7, wherein the hardware compensator is further configured to multiply the second phase by the phase gain to obtain a third phase.

9. The controller according to claim 6, wherein the hardware compensator is further configured to generate the phase shift for the RF inverter controller in response to an update signal from the RF inverter controller.

10. The controller according to claim 8, wherein the hardware compensator further includes a limiter configured to limit the third phase within a predetermined range.

11. The controller according to claim 10, further comprising a scale configured to scale the third phase and provide the scaled third phase as the phase shift to the RF inverter controller.

12. The controller according to claim 1, wherein the RF inverter is further configured to adjust average power of the first and second electrosurgical waveforms based on the phase shift, the phase shift being from about zero to about pi radian.

13. The controller according to claim 1, wherein the signal processor is further configured to decimate and filter sensed voltage and current waveforms of the first and second electrosurgical waveforms to provide first and second path data to the software compensator.

14. An electrosurgical generator comprising:
    a radio frequency (RF) inverter including an H-bridge configured to generate a first electrosurgical waveform from a first pair of switches of the H-bridge and a second electrosurgical waveform from a second pair of switches of the H-bridge;
    a plurality of sensors coupled to the RF inverter and configured to sense a voltage waveform and a current waveform of the first and second electrosurgical waveforms;
    a plurality of analog-to-digital converters (ADCs) configured to digitally sample the sensed voltage and current waveforms; and
    a controller coupled to the plurality of ADCs, the controller including:

a signal processor configured to output a measured value of at least one of a voltage, a current, or a power of the first and second electrosurgical waveforms;

a software compensator configured to generate a desired value for at least one of the voltage, the current, or the power of the first and second electrosurgical waveforms;

a hardware compensator configured to generate a phase shift between the first and second electrosurgical waveforms based on the measured value and the desired value; and an RF inverter controller configured to generate a pulse-width modulation (PWM) signal based on the phase shift to control the RF inverter.

15. An electrosurgical generator comprising:

a power supply configured to output high voltage direct current (HVDC) power;

a radio frequency (RF) inverter coupled to the power supply, wherein the RF inverter includes an H-bridge configured to generate a first electrosurgical waveform from a first pair of switches of the H-bridge and a second electrosurgical waveform from a second pair of switches of the H-bridge;

a plurality of sensors configured to sense a voltage waveform and a current waveform of the first and second electrosurgical waveforms;

a plurality of analog-to-digital converters (ADCs) configured to digitally sample the sensed voltage and current waveforms; and a controller coupled to the plurality of ADCs, the controller including:

a signal processor configured to output a measured value of at least one of a voltage, a current, or a power of the first and second electrosurgical waveforms based on the digitally sampled voltage and current waveforms;

a HVDC setpointer configured to set a desired value for the HVDC power; and an RF inverter controller configured to generate a pulse-width modulation (PWM) signal having a fixed phase for a phase between the first and second electrosurgical waveforms to control the RF inverter based on the desired value.

16. The electrosurgical generator according to claim 15, wherein the fixed phase is in a range where the RF inverter operates in zero voltage switching.

17. The electrosurgical generator according to claim 15, wherein the signal processor is further configured to calculate a phase shift.

18. The electrosurgical generator according to claim 17, wherein the signal processor is further configured to compare the phase shift with the fixed phase.

19. The electrosurgical generator according to claim 18, wherein the HVDC setpointer is further configured to decrease the desired value for the HVDC power when the phase shift is less than the fixed phase.

20. The electrosurgical generator according to claim 18, wherein the HVDC setpointer is further configured to increase the desired value for the HVDC power when the phase shift is greater than a threshold.

* * * * *